United States Patent
Ramer et al.

(10) Patent No.: US 11,287,315 B2
(45) Date of Patent: Mar. 29, 2022

(54) INDICATION OF ULTRAVIOLET (UV) LIGHT INTENSITY USING A LUMIPHORE

(71) Applicant: ABL IP HOLDING LLC, Conyers, GA (US)

(72) Inventors: David P. Ramer, Reston, VA (US); Januk Aggarwal, Alexandria, VA (US); Guan-Bo Lin, Manassas, VA (US); Gregory Malone, Sterling, VA (US); Sean P. White, Sterling, VA (US)

(73) Assignee: ABL IP HOLDING LLC, Conyers, GA (US)

( * ) Notice: Subject to any disclaimer, the term of this patent is extended or adjusted under 35 U.S.C. 154(b) by 115 days.

(21) Appl. No.: 16/848,226

(22) Filed: Apr. 14, 2020

(65) Prior Publication Data
US 2021/0318168 A1    Oct. 14, 2021

(51) Int. Cl.
*A61L 2/10*      (2006.01)
*G01J 1/38*      (2006.01)
(Continued)

(52) U.S. Cl.
CPC ............ *G01J 1/429* (2013.01); *A61L 2/10* (2013.01); *G01J 1/38* (2013.01); *G01J 1/58* (2013.01); *A61L 2202/11* (2013.01)

(58) Field of Classification Search
CPC .......... A61B 2/10; A61B 2202/11; G01J 1/38; G01J 1/429; G01J 1/58; A61L 2/10; A61L 2202/11
See application file for complete search history.

(56) References Cited

U.S. PATENT DOCUMENTS 6,393,038 B1    5/2002  Raymond et al.
8,481,985 B2    7/2013  Neister
(Continued)

OTHER PUBLICATIONS

UV-C Dosimeters by Intellego Technologies—See Your Success with UVC Disinfection, © 2020, https://uvcdosimeters.com/, downloaded Sep. 24, 2020, 7 pages.
(Continued)

*Primary Examiner* — Mark R Gaworecki
(74) *Attorney, Agent, or Firm* — RatnerPrestia

(57) ABSTRACT

A ultraviolet (UV) intensity indicator might use a UV responsive lumiphore to provide a converted, visible light level proportional to received UV light intensity for comparison to a visible brightness reference. For a desired UV intensity, the converted light should normally appear at least as bright as the reference light. For undesired UV, e.g. in a harmful wavelength range, the converted light should appear dimmer than the reference for normal operation and/or appear as bright as or brighter than the reference during excessive emission of the potentially hazardous UV emission. Alternatively, saturable lumiphores may provide different color outputs responsive to UV intensities for comparison to a multi-colored reference. Other examples contemplate use of a lumiphore to convert UV light to provide a visible light input to a visible light meter, such that an illuminance or brightness measurement by the meter gives a proportional representation of intensity of the UV light.

23 Claims, 8 Drawing Sheets

(51) Int. Cl.
  *G01J 1/42* (2006.01)
  *G01J 1/58* (2006.01)

(56) References Cited

U.S. PATENT DOCUMENTS

| | | | |
|---|---|---|---|
| 8,753,575 | B2 | 6/2014 | Neister |
| 8,975,605 | B2 | 3/2015 | Neister |
| 9,700,642 | B2 | 7/2017 | Neister |
| 2010/0187426 | A1* | 7/2010 | Young .................... G01J 1/429 |
| | | | 250/370.07 |
| 2015/0335246 | A1 | 11/2015 | Rains, Jr. et al. |
| 2018/0368221 | A1 | 12/2018 | Johnson et al. |
| 2019/0247528 | A1 | 8/2019 | Rodriguez |
| 2020/0073199 | A1 | 3/2020 | Lin et al. |
| 2020/0244044 | A1 | 7/2020 | Ramer et al. |

OTHER PUBLICATIONS

Brimrose Corp., "Free Space Acousto-Optic Modulators," https://brimrose.com/acousto-optic-modulators, downloaded Aug. 8, 2018, 6 pages.
Manuela Buonanno et al., "Germicidal Efficacy and Mammalian Skin Safety of 222-nm UV Light," HHS Public Access, Author manuscript, Radiat. Res., Apr. 2017, 187(4):483-491, 18 pages.
Kavita Devi et al., "Tunable, continuous-wave, ultraviolet source based on intracavity sum-frequency-generation in an optical parametric oscillator using BiB3O6", © 2013 Optical Society of America, Oct. 21, 2013, vol. 21, No. 21, pp. 24829-24836, 8 pages.
Zhi Fang et al., "Deep-Ultraviolet Nonlinear Optical Crystal Cs2Al2(B3O6)2O: A Benign Member of the Sr2Be2(BO3)2O Family with [Al2(B3O6)2O]2—Double Layers," Chemistry—A European Journal, vol. 24, Issue 31, Apr. 15, 2018, 8 pages.
Far-UV Sterilray—Superior UV Disinfection, "Far-UV Sterilray™ Technology," https://sterilray.com, downloaded Aug. 28, 2018,14 pages.
Hepacart Infection Control Technologies, "Airborne Pathogen Disinfection Module," "The Hepacart® Airborne Pathogen Disinfection Module Featuring: Far-UV Sterilray™ Technology," http://www.hepacart.com/germbuster-air, downloaded Aug. 8, 2018, 5 pages.
Hepacart Infection Control Technologies, "Pathogen Reduction Box 3.0, Hepacart™," http://www.hepacart.com/pathogen-reduction-box-3.0, The Pathogen Reduction Box Featuring Far-UV Sterilray™, downloaded Aug. 8, 2018, 4 pages.
High Energy Ozone, LLC—UV Sterilization Technology, "Technology for Improving Health," https://heo3.com/, downloaded Aug. 8, 2018, 14 pages.
James Johnson, "Selection of Materials for UV Optics," Opti 521, Dec. 1, 2008, 6 pages.
Sheng Liu et al., "Resonantly Enhanced Second-Harmonic Generation Using III-V Semiconductor All-Dielectric Metasurfaces," Nano Letters, 2016, 16(9), 5426-5432, 30 pages.
Min Luo et al., "M2B10O14F6 (M=Ca, Sr): The First Two Noncentrosymmetric Alkaline-Earth Fluorooxoborates as the Promising Next-Generation Deep-Ultraviolet Nonlinear Optical Materials," J. Am. Chem. Soc., published Mar. 8, 2018, 6 pages.
Sunil Mittal et al., "Topological Photonic Systems," Optics and Photonics News, May 2018, pp. 37-43, 7 pages.
Ocular PD LLC, "OcularPD Index," Copyright © 2018 Ocular PhotoDisinfection LLC, http://ocularpd.com/, downloaded Aug. 8, 2018, 1 page.
Pathogen Path Consulting LLC, "Air, Surface and Liquid Disinfection," http://www.far-vu.com/, downloaded Aug. 8, 2018, 5 pages.
Behrooz Semnani et al., "Graphene-Integrated Plasmonic Structure for Optical Third Harmonic Generation," IEEE Journal of Selected Topics in Quantum Electronics, vol. 23, No. 1, Jan./Feb. 2017, 12 pages.
Guoqiang Shi et al., "Finding the Next Deep-Ultraviolet Nonlinear Optical Material: NH4B4OO6F," ACS Publications, © XXXX American Chemical Society, J. Am. Chem. Soc., Jul. 20, 2017, 4 pages.
Chawin Sitawarin et al., "Inverse-designed photonic fibers and metasurfaces for nonlinear frequency conversion [Invited]," Photonics Research, vol. 6, No. 5, May 2018, 8 pages.
United Crystals, "Non-linear Optical Crystal Overview," https://www.unitedcrytals.com/NLOCOverview.html, downloaded Aug. 7, 2018, 2 pages.
United Crystals, "Properties of KDP, DKDP and ADP Crystal," https://unitedcrystals.com/KDPProp.html, downloaded Jul. 16, 2018, 2 pages.
Cheng Wang et al., "Ultrahigh-efficiency second-harmonic generation in nanophotonic PPLN waveguides," Howard Univeristy, Washington, DC, dated Oct. 23, 2018, arXiv:1810.09235v1 [physic.app-ph] Sep. 24, 2018, 5 pages.
Nils Weber et al., "Double resonant plasmonic nanoantennas for efficient second harmonic generation in zinc oxide," Physical Review, B 95, 205307, (2017), Department Physik, universitat Paderborn, 33098 Paderborn, Germany, published May 24, 2017, 6 pages.
Wikipedia, "Acousto-optic modulator," https://en.wikipedia.org/wiki/Acousto-optic_modulator, downloaded Aug. 8, 2018, 4 pages.
Wikipedia, "Optical frequency multiplier," https://en.wikipedia.org/wiki/Optical_frequency_multiplier, downloaded Jul. 16, 2018, 1 page.
Wikipedia, "Second-harmonic generation," https://en.wikipedia.org/wiki/Second-harmonic_generation, downloaded Jul. 16, 2018, 10 pages.
Wikipedia, "Sum-frequency generation," https://en.wikipedia.org/wiki/Sum-frequency_generation, downloaded Jul. 16, 2018, 2 pages.
Wikipedia, "Ultraviolet germicidal irradiation," https://en.wikipedia.org/wiki/Ultraviolet_germicidal_irradiation, Jul. 25, 2018, 9 pages.
Jianchang Yan et al., "Recent progress of research on III-nitride deep ultraviolet light-emitting diode," Scientia Sinica Physica, Mechanica & Astronomica, phys.scichina.com, Science China Press, 2015, 45:067303, https://www.researchgate.net/publication/277921487, Jan. 2015, 21 pages.
Ford Burkhart, "In the War on Opioids 525-nm LEDs Offer Hope," SPIE Copyright © 2019, Oct. 1, 2019, 3 pages.

* cited by examiner

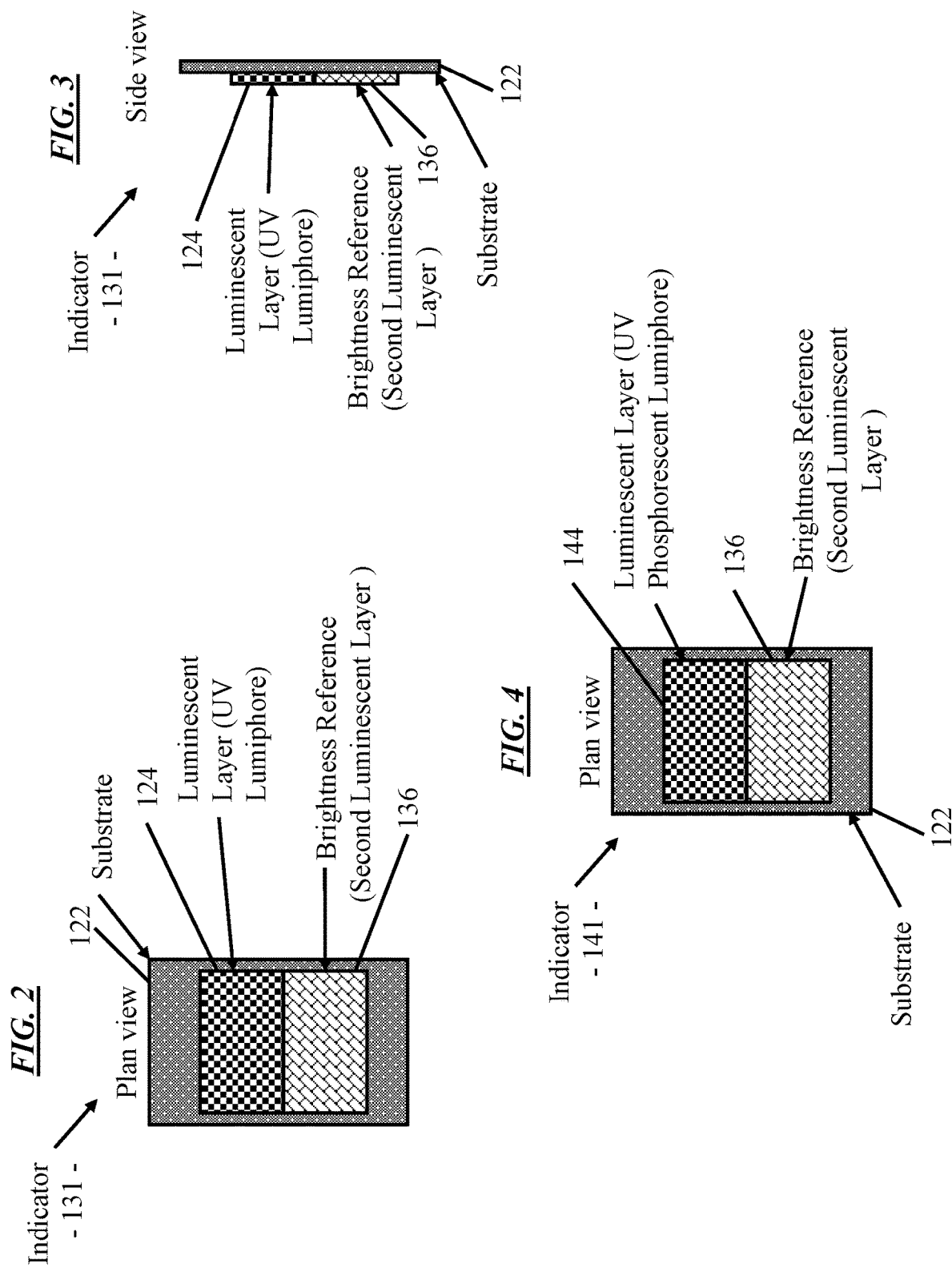

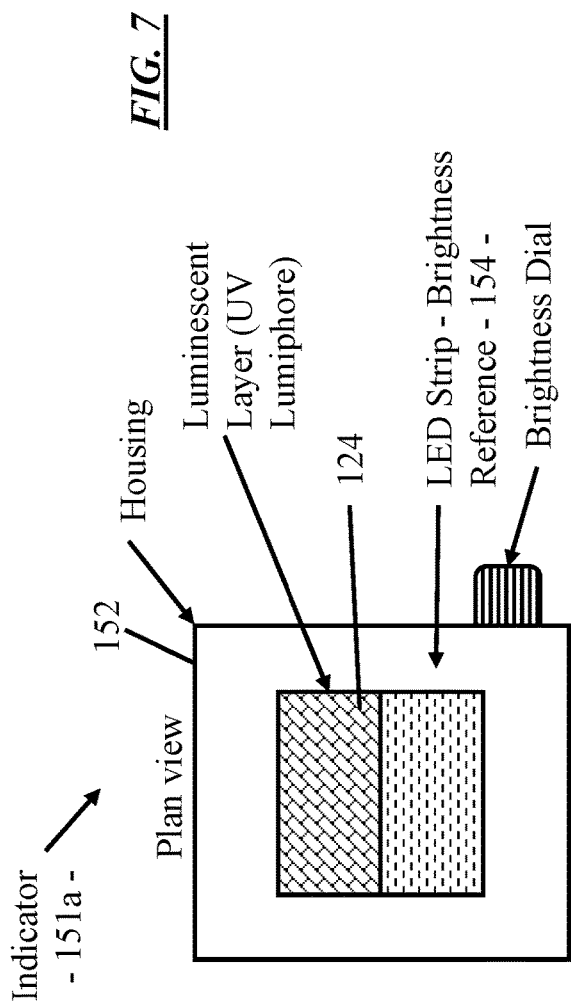
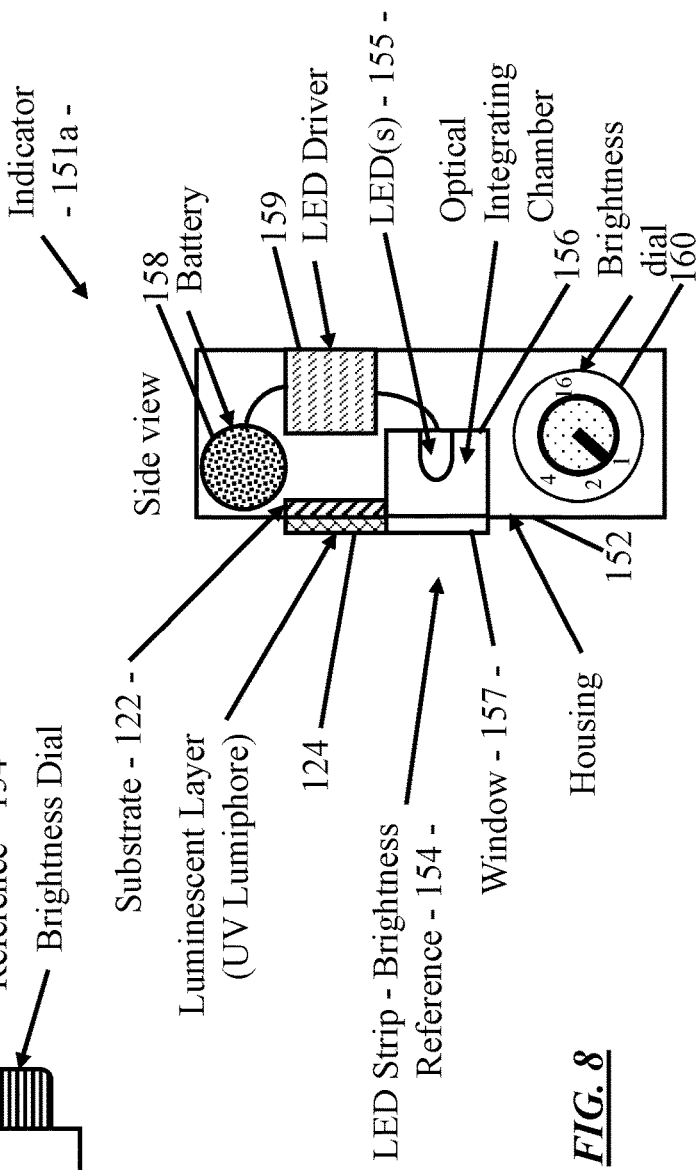

INDICATION OF ULTRAVIOLET (UV) LIGHT INTENSITY USING A LUMIPHORE

TECHNICAL FIELD

The present subject matter relates to devices and techniques to use a lumiphore responsive to ultraviolet (UV) light as part of an indication of UV light intensity, for example, for indicating intensity of UV cleansing light emission from a luminaire that also provides general illumination light output.

BACKGROUND

There have been proposals to incorporate ultraviolet light sources into luminaires that also provide general illumination. For example, there have been various proposals to incorporate, in general lighting equipment, light sources specifically configured to deactivate bacteria, such as Methicillin-Resistant *Staphylococcus Aureus* (MRSA) in the air or on work surfaces, tables, sinks, floors etc. Some proposals have used a single source to generate somewhat white light and light specifically configured to deactivate bacteria, in a manner such that the combined light is suitable for general illumination. Other proposals have incorporated white light sources and disinfection light sources together in one luminaire, including some implementations with independent intensity control of the two different types of sources. Some examples of such equipment have utilized light in a wavelength range that includes at least a portion in the humanly visible spectrum for the sanitation illumination service, e.g. sanitation light having a maximum peak at a wavelength in a range of 400 nanometers (nm) to 450 nm, which may be perceptible as visible light during sanitation operations. Other types of lighting equipment providing a sanitation illumination function or service, however, may utilize appropriate wavelengths in the range from 180 nm to 380 nm in the ultraviolet (UV) portion of the spectrum that is not visible to a human during a sanitation operation. At least some UV wavelengths appear to be more efficacious for sanitation than visible wavelengths. Although some UV wavelengths (e.g. in the range of 207 nm to 225 nm) may have little or no harmful effect on human occupants, other UV wavelengths suitable for sanitation may be harmful to the people in the area.

UV light for sanitation or other functions, however, is not visible. Unlike general illumination with visible like, a person in or entering a space being treated might not realize that a luminaire is outputting UV light. Hence, a controller might operate an electronic indicator to signal a person that the UV light source is active. In another approach, a UV sensitive lumiphore, such as a phosphor that is responsive to UV of the appropriate wavelength(s), might be positioned in the room to emit visible light and thus signal a person a luminaire is outputting UV light. A pulsed operation of the UV output prior to start of a cleansing cycle may also cause the lumiphore to flash (see e.g. paragraph 0079 of Applicant's published US Patent Application Publication No. 2015/0335246 A1).

For many UV applications, such as cleansing, effectiveness requires at least a certain minimum intensity of the applied UV light. For example, to ensure effective cleansing of a surface in a room in a hospital or the like, it may be necessary to apply UV of a particular intensity for a specific duration of time. The application of sufficient intensity over a specific duration serves to apply a cumulative amount of UV light energy so as to deactivate or kill bacteria or other harmful microorganisms in the air or on the surface(s) in the illuminated space.

When initially installed, a luminaire with UV emission capability may be constructed or calibrated to provide UV output at or above the requisite cleansing intensity, and an installer may need to measure the UV output to ensure appropriate intensity per the specifications for the luminaire. From time to time after installation, it may be desirable to recheck the UV output to ensure that the intensity remains at or above the level required for effective cleansing. Although light meters for general illumination in the visible light range of the spectrum are common, most such meters measure brightness or illuminance for visible light only. Light meters capable of measuring intensity of light in the UV range, however, are complex and expensive.

SUMMARY

Hence a need exists for cost effective technology to determine if a UV light output meets a particular intensity criteria. For example, a simple device might provide a converted, visible light level proportional to the UV light intensity for easy comparison to a visible illuminance reference. For a desired UV emission, the converted light should appear as bright as or brighter than the reference for normal operation. For an undesired UV emission, e.g. in a harmful wavelength range, the converted light may appear dimmer than the reference for normal operation and/or appear as bright as or brighter than the reference for an unsafe condition of excessive emission of the potentially hazardous UV emission. Other examples contemplate conversion of UV light to provide a visible light input to a visible light meter, such that an illuminance or brightness measurement by the meter gives a proportional representation of intensity of the UV light.

In an example, an indicator includes a substrate and a luminescent layer supported by the substrate, configured for exposure of at least a portion of the luminescent layer to light from a luminaire. The luminaire is capable of emitting ultraviolet (UV) light having a dominant wavelength in a range from 180 nm to 380 nm. The luminescent layer has a passively activated lumiphore of a type that converts any received UV light that is in at least a portion of the 180 nm to 380 nm UV wavelength range to light having one or more dominant wavelengths in the visible light range. The indicator also includes a brightness reference mounted in visible proximity to the luminescent layer. The brightness reference is configured to produce (e.g., by emitting, reflecting, or a combination of emitting and reflecting) visible light of a predetermined intensity for comparison to intensity of visible converted light from the passively activated lumiphore during reception of the UV light by the passively activated lumiphore.

In another example, an indicator includes a substrate and at least one luminescent layer supported by the substrate, configured for exposure of at least a portion of the one or more luminescent layers to light from a luminaire. The luminaire is capable of emitting ultraviolet (UV) light having a dominant wavelength in a range from 180 nm to 380 nm. In this example, the at least one luminescent layer includes first and second passively activated saturable lumiphores. The first passively activated saturable lumiphore is configured to saturate and convert received UV light up to a first intensity to first visible light. The first visible light causes the luminescent layer to output visible light of a first color characteristic. The second passively activated lumiphore is configured to convert received UV light exceeding the first intensity to second visible light. The second intensity is higher than the first intensity. The second visible light or a combination of the first visible light and the second visible light causes the luminescent layer to output visible light of a second color characteristic, wherein the second color characteristic is visibly different from the first color characteristic. This example indicator also includes a multi-colored brightness reference, mounted in visible proximity to the at least one luminescent layer; and that multi-colored brightness reference includes first and second references. The first reference is configured to emit light at least substantially of the first color characteristic in a first region of the multi-colored brightness reference; and the second reference is configured to emit light at least substantially of the second color characteristic in a second region of the multi-colored brightness reference.

In another example, a measurement system includes a light meter having an optical input and a user output, and a luminescent layer configured for optical coupling to the optical input of the light meter. The luminescent layer has a passively activated lumiphore that converts any received UV light in at least a portion of the 180 nm to 380 nm UV wavelength range to light having one or more dominant wavelengths in the visible light range. The light meter is configured to measure intensity of the visible converted light from the passively activated lumiphore received through the optical input and provide a representation of the measured intensity via the user output as a representation of intensity of the received UV light.

Another example relates to a method that may involve a luminaire emitting visible light for general illumination of a space. The luminaire also emits UV light having a dominant wavelength in a range from 180 nm to 380 nm so as to implement a sanitation application in the space. The method further entails exposing a luminescent material to the UV light emission from the luminaire in the space. The luminescent material includes a passively activated lumiphore configured to convert received UV light in at least a portion of the 180 nm to 380 nm UV wavelength range to light having one or more dominant wavelengths in the visible light range. The method further provides, for observation by a user, a basis to determine intensity of the UV light emission from the luminaire based at least in part on intensity of the light having one or more dominant wavelengths in the visible light range from the passively activated lumiphore.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations, by way of example only, not by way of limitations. In the figures, like reference numerals refer to the same or similar elements.

FIGS. 2 and 3 are plan and side views respectively of an example of an indicator using a luminescent layer as the reference.

FIG. 4 is a plan view of another example of an indicator, in which the UV responsive luminescent layer uses a phosphorescent type lumiphore configured to continue emitting visible light after stoppage of UV emission at which time cessation of visible emission indicates a period after stoppage of UV emission at which UV light emission should be restarted (e.g. time for another sanitation cycle).

FIGS. 7 and 8 are plan and side views respectively of another powered example of an indicator, using for example one or more LEDs as the brightness reference and having a user input for receipt of an intensity setting for the LED based light source to adjust the brightness of the reference.

DETAILED DESCRIPTION

Figure 1:
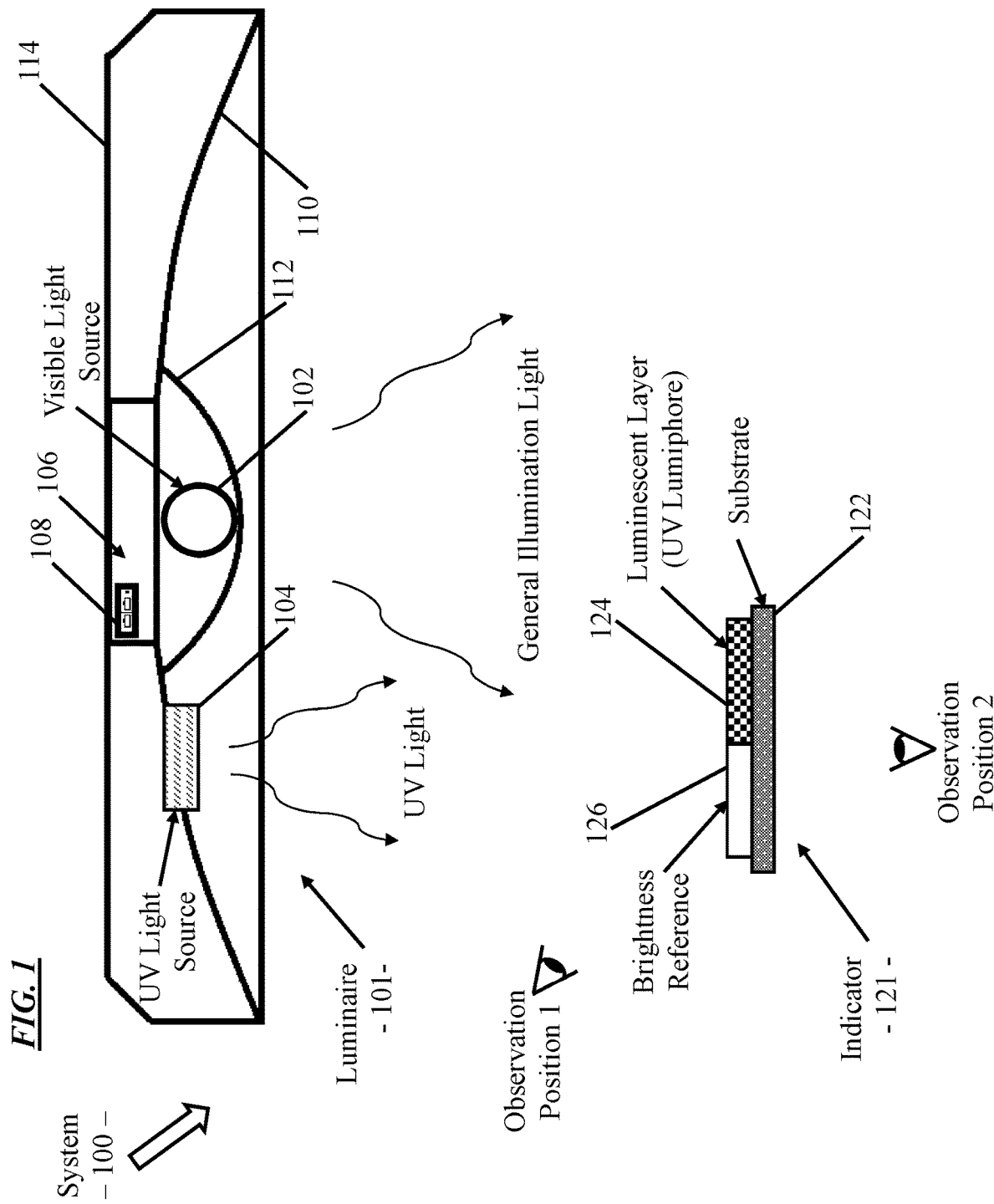
FIG. 1 illustrates a system including a luminaire that produces general illumination light and UV light as well as a UV light intensity indicator with a luminescent layer positioned to respond to the UV light output from the luminaire.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Various examples disclosed herein relate to techniques to use a lumiphore responsive to ultraviolet (UV) light and an associated visible reference to provide an indication of UV light intensity. In one or more alternate examples, the UV sensitive lumiphore may be coupled in front of the input of a visible light meter to supply visible converted light to the meter for intensity measurement. The intensity indication or measurement, for example, may relate to output intensity of UV light from a luminaire that also provides general illumination light output. For purposes of most of the discussions below, it is assumed that the example UV emissions are intended for a sanitation or cleansing function in the space illuminated by light from the luminaire, e.g. to deactivate or kill bacteria or other microorganisms in the illuminated space.

The example luminaires that provide sanitation lighting described below output UV light having a dominant wavelength in the range of 180 nm to 380 nm, most often in the lower parts of that range. The UV sanitation light, for example, may have a dominant wavelength in the range of 207 nm to 225 nm, such as a 220 nm or 222 nm dominant wavelength. UV sanitation light in the 207 nm to 225 nm range may have little or no harmful effect on human occupants. Other UV wavelengths from 225 nm to 380 nm (e.g. in a band centered around 260 nm as the dominant wavelength) also are suitable for sanitation but are more likely to be harmful to the people in the area. There are also sanitation lighting wavelengths between 380 nm to 440 nm that the same techniques can be utilized with. Hence, in some examples, an example luminaire described below can output sanitation lighting having a wavelength between 180 nm to 440 nm, such as 380 nm to 440 nm for violet sterilization light.

Hence, a luminescent device for use in an intensity indicator or for intensity measurement includes a substrate and luminescent layer supported by the substrate, which are configured for exposure of at least a portion of the luminescent layer to light from the luminaire. The luminaire emits general illumination light, e.g. white light of typical intensity and color characteristic values for illumination of occupied spaces. The example luminaire also is configured to emit UV light having a dominant wavelength in a range from 180 nm to 380 nm. The luminescent layer includes one or more passively activated lumiphores, e.g. photo luminescent or fluorescent phosphors or the like, responsive to at least a select portion of the UV wavelength range. In some examples, brightness references may also utilize one or more lumiphores to convert visible light or UV light to wavelengths in the visible spectrum suitable for comparison to light from the UV responsive luminescent layer. A phosphor or the like is a passive lumiphore in that it responds to light of the particular wavelength(s) to which it is sensitive but does not require application of electrical power to perform the conversion function. For purposes of this disclosure, passively activated lumiphores also encompass various meta-materials configured to perform similar conversions light from one wavelength to another.

For example, if the luminaire should output UV in a desired range for a relatively safe sanitation application (e.g. UV wavelengths in the range of 207 nm to 225 nm), at least one lumiphore would be sensitive to that range of wavelengths. Alternatively, if the detector is intended to indicate the intensity of more harmful UV, at least one lumiphore would be sensitive to wavelengths outside the desired less harmful range (e.g. undesired wavelengths in some or all of the range of 226 nm to 380 nm). In other examples, the lumiphore(s) may be sensitive to a broader range of UV or to all of the 180 nm to 380 nm range, for example, for use in an overall UV intensity indicator or for an overall UV intensity measurement. In further alternatives, if the lumiphore(s) are broadly sensitive to UV, more precise detection of a particular range may use a filter to limit the UV light applied to the lumiphore(s) to a particular wavelength range (e.g. to the desired range of sanitation emission or to a potentially more harmful UV wavelength range).

The term "luminaire," as used herein, is intended to encompass essentially any type of device that processes energy to generate or supply artificial light, for example, for general illumination of a space intended for use of occupancy or observation, typically by a living organism that can take advantage of or be affected in some desired manner by the light emitted from the device. However, a luminaire may provide light for use by automated equipment, such as sensors/monitors, robots, etc. that may occupy or observe the illuminated space, instead of or in addition to light provided for an organism. However, it is also possible that one or more luminaires in or on a particular premises have other lighting purposes, such as signage for an entrance or to indicate an exit. In most examples, the luminaire(s) illuminate a space or area of a premises to a level useful for a human in or passing through the space, e.g. general illumination of a room or corridor in a building or of an outdoor space such as a street, sidewalk, parking lot or performance venue. The actual source of general illumination light in or supplying the light for a luminaire may be any type of artificial light emitting component, several examples of which are included in the discussions below. In the examples described herein, each luminaire also is capable of generating UV light. Depending on the intended UV wavelengths, the source of the UV light may be for example one or more LEDs, a gas or vapor discharge lamp, or a visible laser diode in combination with a frequency upconverter to produce UV of the appropriate frequency and wavelength (examples using a laser diode and frequency upconverter are disclosed in Applicant's U.S. patent application Ser. No. 16/121,002 filed Sep. 4, 2018, entitled "Light Frequency Upconversion of Laser Light, For Cleansing").

Terms such as "artificial lighting," as used herein, are intended to encompass essentially any type of lighting that a device produces light by processing of electrical power to generate the light. An artificial lighting device, for example, may take the form of a lamp, light fixture, or other luminaire that incorporates a light source, where the light source by itself contains no intelligence or communication capability, such as one or more LEDs or the like, or a lamp (e.g. "regular light bulb") of any suitable type. The general illumination light output of an artificial illumination type luminaire, for example, may have an intensity and/or other characteristic(s) that satisfy an industry acceptable performance standard for a general lighting application.

The term "coupled" as used herein refers to any logical, optical, physical or electrical connection, link or the like by which signals or light produced or supplied by one system element are imparted to another coupled element. Unless described otherwise, coupled elements or devices are not necessarily directly connected to one another and may be separated by intermediate components, elements or communication media that may modify, manipulate or carry the light or signals.

Light output from the luminaire for general illumination and or any UV application may carry information, such as a code (e.g. to identify the luminaire or its location) or downstream transmission of communication signaling and/or user data. The light based data transmission may involve modulating or otherwise adjusting parameters (e.g. intensity, color characteristic or distribution) of the illumination light output from the device.

Reference now is made in detail to the examples illustrated in the accompanying drawings and discussed below. As shown in FIG. 1, a system 100 includes a luminaire 101 that produces general illumination light and UV light and a UV light intensity indicator 121. The structures, sizes, orientations, distances between the luminaire 101 and the indicator 121, and other illustrated details are shown by way of non-limiting example. The illustrated positions and relationships might represent a situation where the luminaire 101 is a ceiling mounted or recessed light fixture and the indicator 121 is a portable device that may be handheld or placed on a surface in the area illuminated by the luminaire 101 so that the indicator 121 is exposed to UV illumination from the light fixture type luminaire 101.

The example luminaire 101 includes a general illumination light source 102. The source 102 may be any light source used for artificial illumination. Typically, the source 102 produces visible light that a person in or observing the illuminated space might perceive as white light, although there may be various color characteristics provided by different types of sources 102 and/or for different general illumination applications. The light source 102, for example, may produce light of a relatively fixed color characteristic or may instead or in addition provide color or variable color light. Examples of general illumination light source 102 include conventional lamps such as incandescent, halogen, halide or florescent lamps. Examples also include various solid state light emitting devices. Most solid state based luminaires today use some number of light emitting diodes (LEDs).

As illustrated, the example luminaire 101 includes a UV light source 104. UV light may be provided from one location on the luminaire 101 as shown, from two locations on the luminaire 101 or from more locations on the luminaire 101. The exact locations may vary to conform to the structure of the luminaire 101, the intended field of UV light distribution for a particular luminaire product configuration and/or the type of UV light source selected for use in the particular luminaire product.

The UV light source 104 is configured to UV light having a dominant wavelength in a range from 180 nm to 380 nm. Although UV light from the luminaire 101 may be intended for other applications, for discussion purposes the drawings and description below focus of application of the UV light from source 104 for a light-based cleansing/sanitation application, e.g. to deactivate or kill one or more types of potentially harmful microorganisms.

The UV cleansing light, for example, may have a dominant wavelength in the range of 207 nm to 225 nm, such as a 220 nm or 222 nm dominant wavelength. UV sanitation light in the 207 nm to 225 nm range may have little or no harmful effect on human occupants. Other UV wavelengths from 225 nm to 380 nm (e.g. in a band centered around 260 nm) also are suitable for sanitation but are more likely to be harmful to the people in the illuminated space. Depending on the intended UV wavelengths, the source or sources 104 of the UV light may be for example one or more LEDs, a gas or vapor discharge lamp, or a visible laser diode in combination with a frequency upconverter to produce UV of the appropriate frequency and wavelength.

The non-limiting example 101 of the luminaire assumes a relatively 'smart' luminaire implementation having communication capability for control of the general illumination and/or cleansing capabilities of the example luminaire 101. Hence, the example also includes an access area 106 for wired communication connectors, such as RJ45 connectors 108. If the luminaire 101 incorporates wireless communication capability, connectors 108 and the access area 106 may be omitted. Power connections to AC mains or to DC lines to a separately located driver (not shown) may also be provided in the access area 106 or elsewhere on the luminaire 101. Alternatively, the driver and communications circuits may be incorporated into the luminaire 101 itself.

The example luminaire 101 includes a reflector 110 and a diffuser 112 optically coupled to the output of the light source 102. The reflector 110 and the diffuser 112 may at least partially enclose the light source 102, as illustrated by way of example in the drawing. The reflector 110 and the diffuser 112 distribute at least the general illumination light from the source 102 in a space or on an area intended for illumination, in accordance with a distribution specification for the particular luminaire configuration. A wide variety of materials and structures may be used to implement the reflector 110 and the diffuser 112. The location and optical relationship of the reflector 110 and the diffuser 112 relative to the source 102 and to each other are shown by way of non-limiting example only; and it should be apparent that other arrangements may be suitable to particular artificial illumination applications. Also, depending on the particular general illumination application of a luminaire and/or the intended aesthetics of the luminaire design, one or both of the reflector 110 and the diffuser 112 may be omitted.

In the example of FIG. 1, the luminaire 101 also includes a housing 114. The housing may have any particular structure and/or aesthetic design that is suitable to the intended location, mounting location, illumination application specifications, and cleansing function.

The illuminated space (e.g. generally below the luminaire 101 in the illustrated example) may be any room, hallway, or the like of a building or an outdoor area, where illumination and cleansing to deactivate or kill microorganisms may be desirable. The luminaire 101 typically is installed as a fixture or positioned in a space as a floor or table lamp, for long term operation. The indicator 121 also may be located or installed for exposure whenever the luminaire 101 is operating. In many cases, however, the indicator 121 may be carried by a person checking performance of a number of similar luminaries located about a premises or kept in a drawer or cabinet in the space or elsewhere at the premises. The luminaire may just be a light source that only emits UV wavelength light.

The example indicator 121 in the system 100 includes a substrate 122 and a luminescent layer 124 supported by the substrate, configured for exposure of at least a portion of the layer 124 to the UV light emitted from the luminaire 101. However, system 100 does not need to include the substrate. The lumiphore can be self-supporting or embedded into a support structure, such as a polymer (e.g., glue, adhesive, plastic, silicon, etc.); ceramic; and/or other materials for support. The example illustrates an arrangement (e.g. without a housing or protective cover or the like) in which the upper surface of the luminescent layer 124 may be exposed to UV light from light source 104 when the indicator 121 is held horizontally or placed on a horizontal surface below the downlight example of the luminaire 101. If included in a housing or the light with a aperture to allow exposure of a surface of the luminescent layer 124, somewhat less of the surface of the luminescent layer 124 intended to face toward light output of the luminaire 101 may be available for exposure to the UV light emitted from the luminaire 101.

The luminescent layer 124 has at least one passively activated lumiphore of a type that converts any received UV light during exposure, which is in at least a portion of the 180 nm to 380 nm UV wavelength range, into light having one or more dominant wavelengths in the visible light range. The lumiphore may be selected to have an excitation range covering substantially all of the 180 nm to 380 nm wavelength range. In other cases, the passively activated lumiphore may be selected for a range limited to the desired UV range for a particular cleansing application, e.g. in the 207 nm to 225 nm range for relatively safe cleansing or in the 226 nm to 380 nm range for UV cleansing that may be potentially harmful.

The layer 124 may be formed in the substrate 122 to extend somewhat inward from the surface of the substrate intended for receiving light from the luminaire 101, for example, by doping a phosphor or other suitable lumiphore into the material forming the substrate 122. Alternatively, as shown by way of non-limiting example, the luminescent layer 124 may be formed on a surface of the substrate 122 intended to face the UV output of the luminaire 101, for example, as a paint or other type of coating.

The indicator 121 also includes a brightness reference 126 mounted in visible proximity to the luminescent layer 124. The brightness reference 126 is configured to produce (e.g., by emitting, reflecting, or a combination of emitting and reflecting) visible light of a predetermined intensity for comparison, e.g. by an observer/user of the indicator 121, to the intensity of visible converted light from the passively activated lumiphore in the layer 124 during exposer/reception of the UV light from the luminaire 101 by the passively activated lumiphore.

As will be apparent from discussion of later examples, the brightness reference 126 may be implemented in a variety of different ways. For convenience, FIG. 1 shows an example in which brightness reference 126 is mounted or formed on the same surface as a coating that forms the luminescent layer 124. It should be apparent, however, that other examples may implement or locate the brightness reference 126 in other ways, e.g. behind the substrate 122 (visible through the substrate or through a window/aperture in the substrate) or beside the substrate 122.

Some luminaires have used remote phosphors or the like to modify the visible light output, for example, to convert UV and/or blue light to wavelengths in the visible range so that the overall light output has a desirable white color characteristic, e.g. a 'warm' white appearance. The indicator 121 with the luminescent layer 124 is not so integrated into the luminaire 101 that the lumiphore in the layer 124 modifies the overall visible light output from the luminaire 101. The luminescent layer 124 instead provides a visible indication of the intensity of the UV light output from the luminaire 101. Some or all of the indicator 121, particularly the luminescent layer 124, might be located on the luminaire 101 at some position where a user might observe the converted light output from the luminescent layer 124 and concurrently observe the output of the brightness reference 126 while looking toward some portion of the luminaire 101. Typically, however, the indicator 121 takes the form of a separate device; and in many cases, the indicator 121 may be portable rather than fixedly mounted in the vicinity of the luminaire 101.

As used herein, a "lumiphore" includes one or more materials, such as a phosphor, a nano-phosphor, a phosphorescent, and/or a meta material, etc. that converts light from one wavelength to another. This light wavelength conversion may be visible to an observer/user as a glow (e.g., fluorescence). Phosphor materials are a general class of lumiphores that convert light of one wavelength to light of another wavelength. A phosphor for converting UV wavelength(s) of light to light of visible wavelength(s) performs a down-conversion (decrease in frequency and/or energy although an increase in wavelength). Different down-converting phosphors, however, have different excitation wavelength ranges and/or have different emission excitation wavelength ranges. The examples of the luminescent layer may use any phosphor with an excitation range including at least a portion of the UV wavelength range and having a desired emission range in the visible portion of the light spectrum (e.g. a selected color output or a selected color temperature white light). Some phosphors may be selected that have an excitation range covering substantially all of the 180 nm to 380 nm wavelength range. In other cases, the phosphors may be selected for a range limited to the desired UV range for a particular cleansing application, e.g. in the 207 nm to 225 nm range for relatively safe cleansing or in the 226 nm to 380 nm range for UV cleansing that may be potentially harmful. The lumiphore in the layer 124, however, may use other materials. Other examples or lumiphores include phosphorescent materials, nano-phosphors and certain down-conversion type meta materials.

In some examples, the brightness reference 126 may utilize a similar lumiphore. The intensity of brightness reference 126 depends on the amount of visible light that shines upon it and this brightness can be confirmed with a visible light illuminance meter, which is commonly owned by lighting professionals, such as the Konica-Minolta CL-200 that measures foot-candles or lux. In such examples, if a calibrated UV light source is included in the indicator, the brightness reference lumiphore may be similar to the lumiphore included in the luminescent layer 124 but located/constructed to convert light from the included calibrated UV light source. In other implementations, the brightness reference 126 may include a lumiphore having an excitation range in the visible portion of the light spectrum, for example, to respond to a portion or all of the color spectrum included in the white light for general illumination output by the luminaire 101.

Many types of glass tend to reduce intensity or block UV light at least for the potentially harmful UV wavelengths. Such glass, however, may pass some or all wavelengths of light in the visible light range. Hence, a glass substrate may also act as a filter to pass light of desired visible wavelengths and block some or all UV wavelengths.

The brightness reference 126, in a simple example, may be a reflector (or exposed section of a reflective implementation of the substrate 122) configured to reflect white general illumination light from the luminaire 101. In such an example, the luminescent layer 124 would include a mixture of lumiphores each having an appropriate UV excitation range but various visible light emission ranges that together convert received UV light to combined visible light that overall appears white. If the color characteristic of the general illumination light output is known or sufficiently calibrated, the combination of lumiphores in the luminescent layer 124 may provide a converted white light having substantially the same color characteristic as the general illumination light reflected by the reference 126, at least to such an extent that a typical human observer is unlikely to perceive differences in color characteristic between light from the layer 124 and light from the reference 126.

Alternatively, the lumiphore in the luminescent layer 124 may provide a converted visible light output of a particular relative saturated color, e.g. red or green or blue, etc. If the brightness reference 126 still uses a reflector, the material of the reflector or an additional filter may be configured to limit the reflected light to substantially the same color as that of the converted light from luminescent layer 124.

An example of operations of the system 100 may include the luminaire 101 emitting visible light for general illumination of the space and the luminaire 101 emitting UV light having a dominant wavelength in the range from 180 nm to 380 nm so as to implement a sanitation application in the space. The emissions may overlap in time, e.g. so that the sanitation is performed while the space is illuminated with white light. Alternatively, the emissions may occur at different times, e.g. so that the sanitation is performed while the space is not illuminated with white light (e.g. while the space is generally dark except possibly for any ambient light from another source). The operations methodology thus may further entail exposing the luminescent material of layer 124 to the UV light emission from the luminaire 101 in the space. The luminescent material includes the passively activated lumiphore, which converts any received UV light in at least a portion of the 180 nm to 380 nm UV wavelength range to light having one or more dominant wavelengths in the visible light range. For observation by a user, the brightness reference 126 in this example provides a basis to determine intensity of the UV light emission from the luminaire based at least in part on intensity of the visible light (e.g. having one or more dominant wavelengths in the visible light range) from the passively activated lumiphore.

In some examples, the passively activated lumiphore in the layer 124 is configured to emit visible light of a predetermined color characteristic, at least when the UV emission is at or above the desired intensity level. For example, the absorber in the top first layer can be a non-visibly emitting saturable absorber. The non-visibly emitting saturable absorber shields the second layer lumiphore, such that the second layer lumiphore starts to glow only after the non-visibly emitting saturable absorber saturates. The non-visibly emitting saturable absorber can include dyes, non-visible phosphors, and/or other saturable absorbers. This would have the advantage of not requiring a brightness reference 126.

Various examples of the brightness reference 126 may be further configured to produce (e.g., by emitting, reflecting, or a combination of emitting and reflecting) visible light of a color characteristic at least substantially similar to the predetermined color characteristic output by the luminescent layer 124. Two color characteristics are sufficiently similar if a typical human observer would consider two lights having such color characteristics to be more of less the same color. Lights or color characteristics that a typical human observer would consider to be different would not be sufficiently similar. Light outputs from the luminescent layer and the brightness references having similar color characteristics, for example, may be white lights of approximately the same color temperature or lights of approximately the same specific recognizable individual color (e.g. both red, both green, or both blue etc.). An alternate example described later regarding FIGS. 14 and 15 uses a luminescent layer having a number of different saturable lumiphores to generate visible light of different color characteristics based on receipt of UV light of different intensities; and the reference in such an example provides corresponding different color reference light outputs.

A human observer often is very good at detecting an intensity difference in such a bipartite arrangement, e.g. where both visible light outputs have substantially the same color characteristic. The system/methodology of FIG. 1 therefore offers a simple and relatively inexpensive technology to enable a user to determine the relative intensity of the UV light output as represented by converted light from the luminescent layer 124 in comparison to the intensity of the light from the reference indicator 126.

For some cleansing application examples, the UV source may remain OFF for substantial periods of time and then activated for a suitable time and intensity to cleanse one or more surfaces in the illuminated space and/or to cleanse the air in the vicinity of the luminaire 101. When the UV light output from the luminaire 101 is OFF, the luminescent layer 124 receives no UV light, and the lumiphore in that layer 124 does not produce a visible light output. The brightness reference 126 may or may not emit visible light even when the UV light is off, depending on the implementation of the reference 126, e.g. whether electrically powered or excited by part of the visible light output from the luminaire 101. When the UV light output from the luminaire 101 is ON and the indicator is positioned so that the luminescent layer 124 receives some of that UV light, the lumiphore in that layer 124 produces a visible light output that may be observed by a person in the vicinity, e.g. by a user of the indicator, and compared visually to light from the brightness reference 126.

The substrate 122 may be a somewhat reflective material relative to at least visible light wavelengths, so that most of the visible light emitted by the luminescent layer 124 is directed into the space roughly between the luminaire 101 and the indicator 121. The brightness reference 126 also would be configured to emit visible reference light into the space roughly between the luminaire 101 and the indicator 121. With such an indicator arrangement, a user might hold the indicator 121 in her hand under the luminaire 101 or place the indicator 121 on a surface that is to be subjected to UV cleansing under the luminaire 101. Then, the user might observe the converted visible light from the luminescent layer 124 and the visible light from the brightness reference 126 from a location such as that shown as example observation position 1 in the drawing.

By way of another example, the substrate 122 may be a somewhat transparent or translucent material relative to at least visible light wavelengths, so that at least a substantial amount of the visible light emitted by the luminescent layer 124 is emitted from the indicator 121 via the substrate 122. The brightness reference 126 also would be configured to emit visible reference light through the substrate 122. With such an indicator arrangement, a user might hold the indicator 121 up for exposure to UV light from the luminaire 101. Then, the user might observe the converted visible light from the luminescent layer 124 and the visible light from the brightness reference 126 from a location such as that shown as example observation position 2 in the drawing.

The downlight orientation of the luminaire 101, the horizontal orientation of the indicator 121 across the relatively vertical light outputs from the luminaire 101 and the possible positions for observing the converted visible light from the luminescent layer 124 and the visible light from the brightness reference 126 are shown in drawing by way of non-limiting examples only.

FIGS. 2 and 3 are plan and side views respectively of an example of an indicator 131 using another (e.g. second) luminescent layer 136 as the brightness reference. The substrate 122 and the luminescent layer 124 (e.g. with a first lumiphore) may be essentially the same as the similarly numbered substrate and luminescent layer in the example indicator 121 of FIG. 1. The second luminescent layer 136 for use in the brightness reference (in indicator 131) is configured to produce the visible light of the predetermined intensity by activation of another one or more lumiphores in that second layer 136. For example, the second luminescent layer 136 may include one or more passively activated lumiphores configured to convert at least some visible light received from the luminaire 101 (FIG. 1) to visible light of a predetermined color characteristic at the predetermined intensity. The lumiphore(s) of the second luminescent layer 136 may be similar phosphor(s) or the like as given by way of example for the lumiphore(s) of the layer 124 above except that that any phosphor or other lumiphore used in the of the second luminescent layer 136 has a wavelength excitation range in the visible spectrum.

FIG. 4 is a plan view of another example 141 of a brightness indicator. The indicator 141 uses a somewhat different type of luminescent layer 144. In that layer 144, the passively activated lumiphore comprises a phosphorescent material configured to discharge over time after ceasing to receive UV light, so as to cease emission of the visible light of a predetermined color characteristic after a predetermined time delay indicative a period after which UV light emission should be restarted. The substrate 122 is similar to the substrate in the earlier examples. The drawing shows a brightness reference 136 similar to that of the example of FIGS. 2 and 3, although the indicator 141 may use any brightness reference as discussed relative to FIG. 1 or as discussed relative to any of the other indicator examples described below.

A number of suitable UV sensitive phosphorescent type phosphors are known that may charge up slowly in response to receipt of UV in the appropriate excitation range and then discharge slowly after UV reception ends. For a cleansing application, for example, an observer may consider the UV intensity appropriate if the visible converted light from the luminescent layer 144 is as bright as or brighter than the light from the brightness reference 136. The observer may consider that a new cleansing UV irradiation cycle is due (and therefore manually re-activate the UV light source) when the luminescent layer 144 appears to no longer be emitting visible converted light (following the delay after cessation of the most recent UV emission cycle for cleansing).

Figure 5:
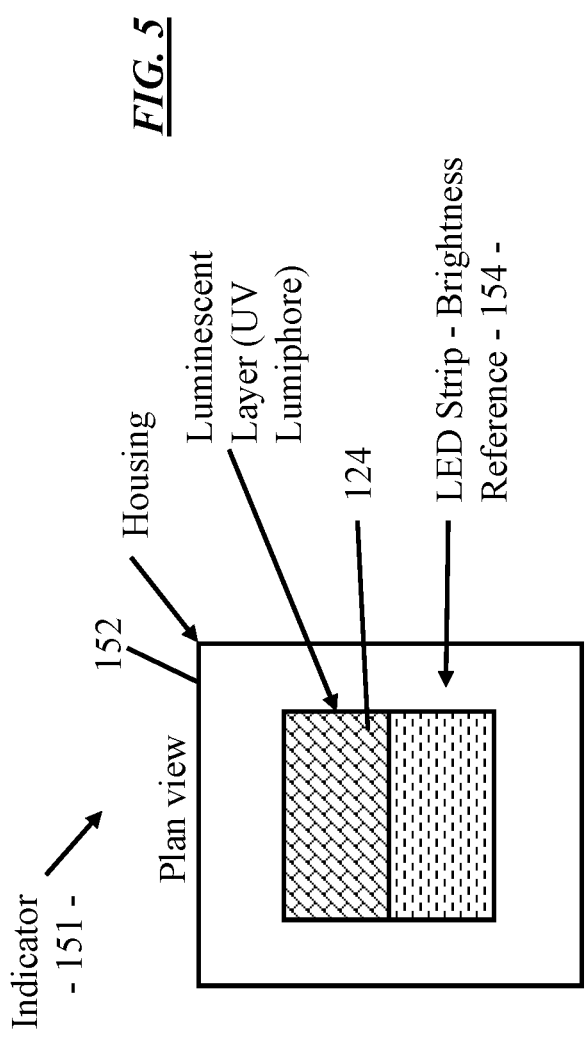
FIGS. 5 and 6 are plan and side views respectively of a powered example of an indicator, using for example one or more light emitting diodes (LEDs) as the brightness reference.
Figure 6:
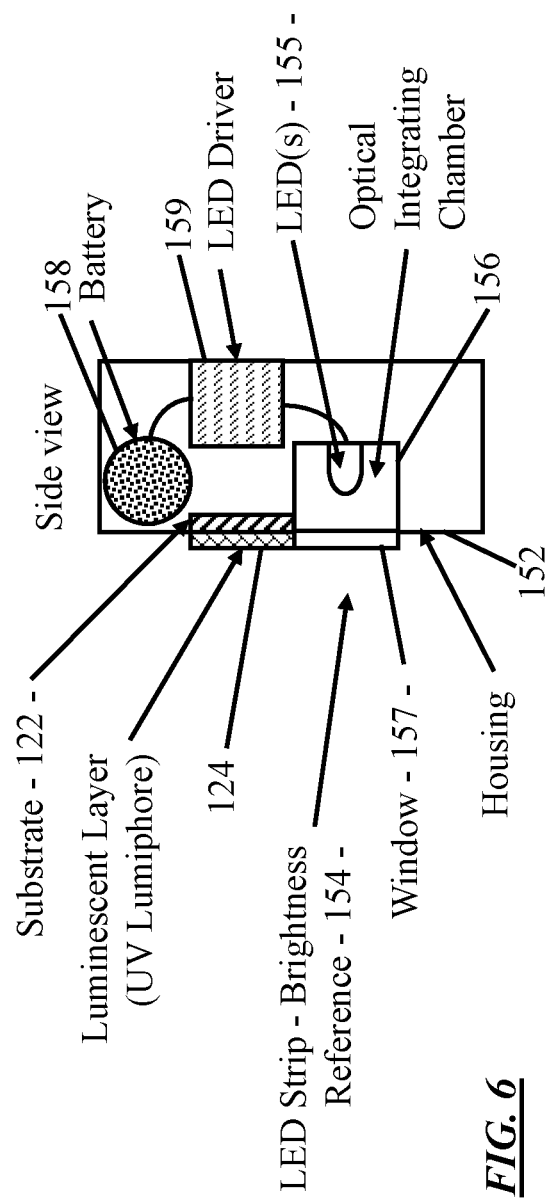

FIGS. 5 and 6 are plan and side views respectively of an indicator, using one or more light emitting diodes (LEDs) as the brightness reference.

The example indicator 151 used in a system like that shown in FIG. 1 includes a substrate 122 and a luminescent layer 124 supported by the substrate, configured for exposure of at least part of a surface of the layer 124 to the UV light emitted from the luminaire. The substrate 122 and the luminescent layer 124 may be implemented as in other examples described herein, except that in the indicator 151, the substrate 122 is shown supported by or part of a housing 152.

The brightness reference in the example indicator 151 uses a suitable form of an artificial light source configured to produce the visible light of the predetermined intensity in response to applied electrical power. Hence, the indicator 151 also includes a corresponding driver circuit configured to apply the electrical power to the light source. The light source of the brightness reference may produce a reference light of a color characteristic substantially similar to the color characteristic produced by the lumiphore(s) of the luminescent layer 124 when excited by received UV.

FIGS. 5 and 6 show an implementation of a power driven brightness reference light source as a light emitting diode LED 154 strip having an output alongside the luminescent layer 124. Although other structures/arrangements may be used to form such a strip 154, the example LED strip 154 shown in FIGS. 5 and 6 includes one or more LEDs 155 mounted in or coupled to a reflective optical integrating chamber 156 in the housing 152 with a light transmissive window 157 across a light output aperture of the chamber 156 (see FIG. 6). The window 157 may be transparent or translucent and/or configured to diffuse light from the one or more LEDs 155.

Hence, the artificial type brightness reference light source is shown as conventional light emitting diodes LED(s), typically one or more LEDs 155 in a row or matrix to provide light output of the strip 154. The artificial light source, however, may be any power driven light source, such as an organic light emitting diode (OLED), or a suitable incandescent, halide or halogen lamp, or the like. In the example illustrated, the reference light source is driven so as to emit a reference light of the appropriate intensity and/or color characteristic so as to allow visual comparison to UV responsive e light output from the luminescent layer 124, similar to operation of the earlier examples. A later example provides different configurations of the brightness reference and the luminescent layer so as to output different colors (see e.g. discussion of FIGS. 14 and 15); and it should be understood that an alternate implementation of that indicator might use a power-driven brightness reference light source with LEDs or other type powered source configured with an appropriate or settable color output.

In the example of FIG. 6, the indicator 151 includes at least one battery 158 of suitable size and capacity to operate the indicator 151. Depending on the number LEDs 155 and the power requirements of the LEDs 155, the indicator 151 may also include a DC to DC type driver circuit 159 to convert the power (e.g. current and/or voltage level) output from the battery 158 to operate the LEDs 155 to output light of a suitable intensity. Alternatively, the driver 159 may draw power from an AC line or from another line source (e.g. USB port) and convert the AC or other type line voltage to suitable DC voltage and current to drive the LEDs 155. User control element(s) for the LED driver 159 and thus the LEDs 155 of the example brightness reference light source, e.g. an ON/OFF switch, are omitted for ease of illustration.

FIGS. 7 and 8 are plan and side views respectively of another battery powered example 151*a* of an indicator, using one or more LEDs 155 in an LED strip 154 as the brightness reference. Most of the elements of the indicator 151*a* are the same as those of the indicator 151 described above and are identified by the same reference numbers as in FIGS. 5 and 6.

The example indicator 151*a*, however, also includes a user input, for receipt of an intensity setting for the LED based light source to adjust the brightness and/or color of the reference light output from the LED strip 154. In these drawings the user input takes the form of a brightness dial 160, although other types of user inputs may be used as alternatives or in addition to the example dial type input 160. The user input may itself regulate power to the LED(s) 155, e.g. if the dial 160 is coupled to a variable resistor or the like in the line carrying current between the LED driver 159 and the LED(s) 155 or in a line between the LED(s) 155 and ground. Alternatively, the brightness dial 160 or other user input may provide a selection input to the LED driver 159 which responds with appropriate adjustment of current and/or voltage applied to the one or more LELDs 155.

Different UV intensities may be used to perform a cleansing application, albeit over corresponding different time intervals intended to achieve a particular cumulative UV exposure dosage. The different input selections provided via the brightness dial 160 or other user input cause the LED strip type brightness reference 154 to output reference light at different levels, which may correspond to different UV output intensities for cleansing over respective time intervals.

The example dial 160 has four input level markings, graded by different time intervals to achieve a cleansing dosage of UV exposure. Lower intensity, typically requires a longer time interval to achieve the cleansing exposure dosage. Hence, in the example, the setting 1 represents the highest intensity setting for the cleansing application; and that setting causes a high luminance level output from the LED strip brightness reference 154. That reference light output level would match a high UV intensity output from the luminaire indicated by the visible light output from the luminescent layer 124, for providing a UV dosage sufficient to kill or deactivate microorganisms in approximately 1 minute of exposure time. The number 2 setting would produce lower reference light output from LED strip 154, but that a level would match a UV intensity output from the luminaire indicated by the visible light output from the luminescent layer 124, for providing a UV dosage sufficient to kill or deactivate microorganisms in approximately 2 minutes of exposure time. The example settings at 4 and 16 in turn would cause the strip 154 to output reference light levels corresponding approximately 4 minutes and 16 minutes of exposure times to achieve the UV exposure dosage intended for the cleansing application.

For a given fixed or pre-set UV output luminance, the adjustment of the dial 160 allows the user to match the intensity of the reference light output via the LED strip 154 with the intensity of visible converted light output from the luminescent layer 124 produced by the received UV light. In such an example, the user may read the corresponding setting number on the dial 160 when the outputs from 124 and 154 approximately match, so as to determine how long to keep the UV light output on at the given level. In an alternative operation where the UV intensity is adjustable, the user may set the dial to a desired time interval, and then control operation of the UV light source in the luminaire to adjust the intensity from the LED strip 154 to match intensity of the visible converted light output from the luminescent layer 124. The user might then turn off the UV light source at the end of the specified time interval.

Figure 9:
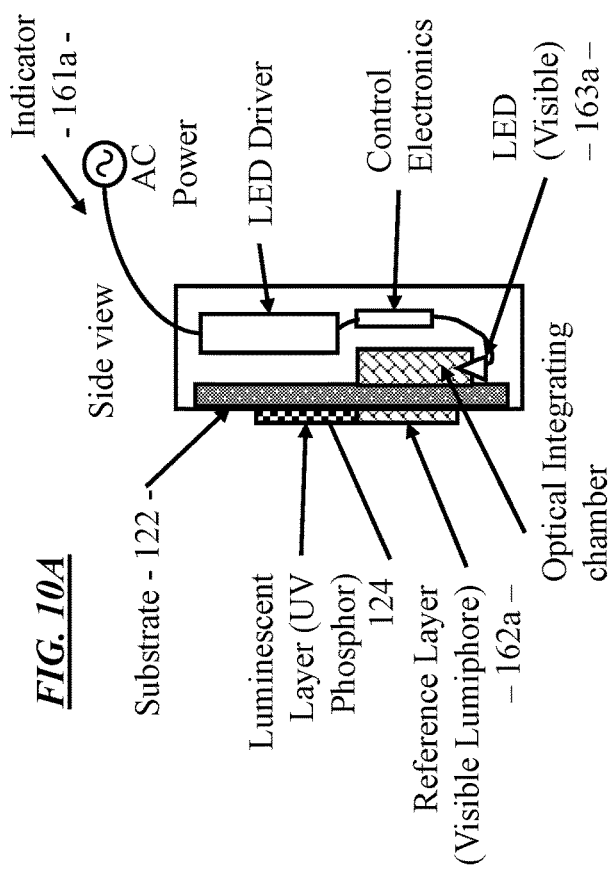
FIG. 9 is a plan view of an example indicator, which uses one or more LEDs or another artificial light source to provide light to a passively activated lumiphore in a luminescent layer forming the brightness reference.
Figure 10A:
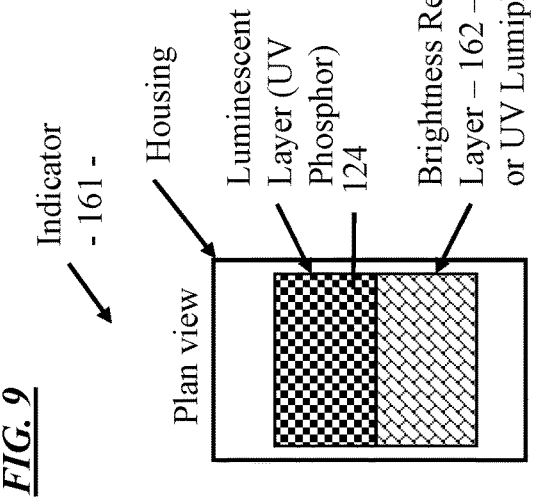
FIGS. 10A and 10B are side views of the indicator of FIG. 9 using different implementations of the brightness reference, in which the indicator of FIG. 10A uses one or more visible color LEDs (e.g. blue or near UV) and a lumiphore responsive to that visible light, and the indicator of FIG. 10B has a brightness reference using a UV light source and a portion of the same layer/lumiphore used to respond to the UV light from the luminaire.
Figure 10B:
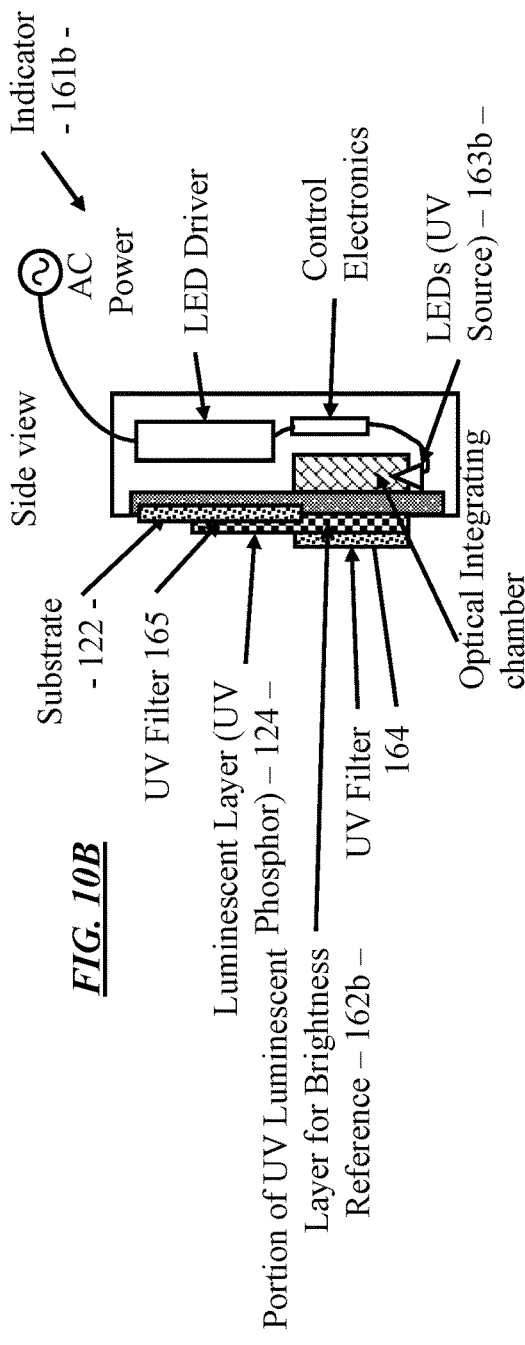

FIG. 9 is a plan view of an example indicator 161, which uses one or more LEDs or another artificial light source to provide light to a passively activated lumiphore to generate light of the brightness reference. FIGS. 10A and 10B show somewhat different configurations 161a or 161b of the indicator 161 (FIG. 9), which use different types of light sources to excite somewhat different implementations 162a or 162b (FIGS. 10A, 10B) of a lumiphore/luminescent layer 162 (FIG. 9) for the brightness reference.

At a high level, the luminescent layer 124, the UV responsive lumiphore(s) of layer 124, the indicator housing, one or more LEDs as an example of the reference light excitation source, the optical integrating chamber and the LED driver may be generally similar to those described above relative to examples shown in FIGS. 5 to 8. Unlike the earlier power driven examples where the LEDs emitted light of the color characteristic intended for the brightness reference output, the particular LEDs 163a, 163b are of different types that emit light to excite respective lumiphores having different excitation ranges. By way of example, the LEDs 163a, 163b are shown coupled somewhat differently to the optical integrating chamber, the LED driver is shown receiving power from AC mains instead of a battery, and the driver is coupled to control electronics, e.g. to provide regulation, timing control and/or control in response to a selection or setting received via a user input (not shown in these figures).

FIGS. 10A and 10B are side views of the indicator of FIG. 9 using different implementations of the brightness reference. In both these examples, the brightness reference includes an artificial light source shown by way of example as one or more of the LEDs 163a or 163b, configured to excite the respective phosphor or other lumiphore so that the luminescent layer 162a or 162b respectively produces the visible light of the predetermined intensity in response to applied electrical power. In one of the illustrated examples (FIG. 10A), the lumiphore/luminescent layer for the brightness reference may be an additional layer on the same substrate 122 as the layer 124 or on a different substrate (not shown). In the other illustrated example (FIG. 10B) the lumiphore/luminescent layer for the brightness reference is a section or portion of the layer 124. The section 163b of the luminescent layer 124 for the brightness reference, however is aligned to receive UV light from the LEDs of UV source 163b.

In FIG. 10A, the brightness reference includes one or more visible color LEDs, e.g. blue or 405 nm or the like in the near UV visible range. The reference in the example of FIG. 10A also includes a lumiphore responsive to that visible light, for example, as part of the illustrated additional luminescent layer 162a. Reference light, similar to such light generated in earlier examples, is produced by conversion of light from the LED(s) 163a into the desired reference light output by lumiphore(s) in the layer 162a for comparison to converted visible light generated by the lumiphore(s) in the layer 124 upon receipt of UV light from the luminaire.

In FIG. 10B, the brightness reference includes a UV light source for example formed by one or more UV emitted LEDs 163b, driven by the applied electrical power from the driver/control electronics. Although there may be an additional luminescent layer to carry UV responsive lumiphore(s), the brightness reference in this example relies on a portion 162b of the luminescent layer 124 and the lumiphore(s) therein to generate reference light in response to excitation by UV light from the UV LEDs 163b (or other implementation of the UV light source) in the indicator 161b. Hence, The UV light source in the indicator may emit approximately the same range of UV wavelengths as the UV light source in the luminaire; or the UV light source in the indicator may emit UV light in a smaller band of wavelengths within the excitation range of the particular one or more lumiphores in the luminescent layer 124. The resulting reference light has the same color characteristic as converted visible light generated by the lumiphore(s) in the layer 124 upon receipt of UV light from the luminaire.

The UV LEDs 163b (or other implementation of the UV light source) in the indicator 161b are positioned to direct UV light to the section 162b of the luminescent layer 124 such that the passively activated lumiphore(s) in that section 162b of the luminescent layer 124 converts UV light from the UV light source into the visible light of the predetermined intensity for the comparison. To prevent excitation by of the lumiphore(s) in section 162b by UV light from the luminaire, the indicator 161b includes a UV blocking filter 164. The filter 164, however, passes visible light in the wavelength range of converted light output by excitation of the lumiphore(s) in the section 162b.

Optionally, the indicator 161b may include an additional UV blocking filter 165 to block UV light that may otherwise pass through the part of the luminescent layer 124 exposed to UV light from the UV source in the luminaire, if necessary to prevent exposure of section 162b to such UV light (e.g. if the wall of the integrating chamber and/or other elements inside the housing would not otherwise prevent such interfering exposure). The filter 164 may also block any UV light that may leak from the chamber from impacting the conversion of light from the luminaire by the lumiphore in the upper region of the layer 124.

Figure 11:
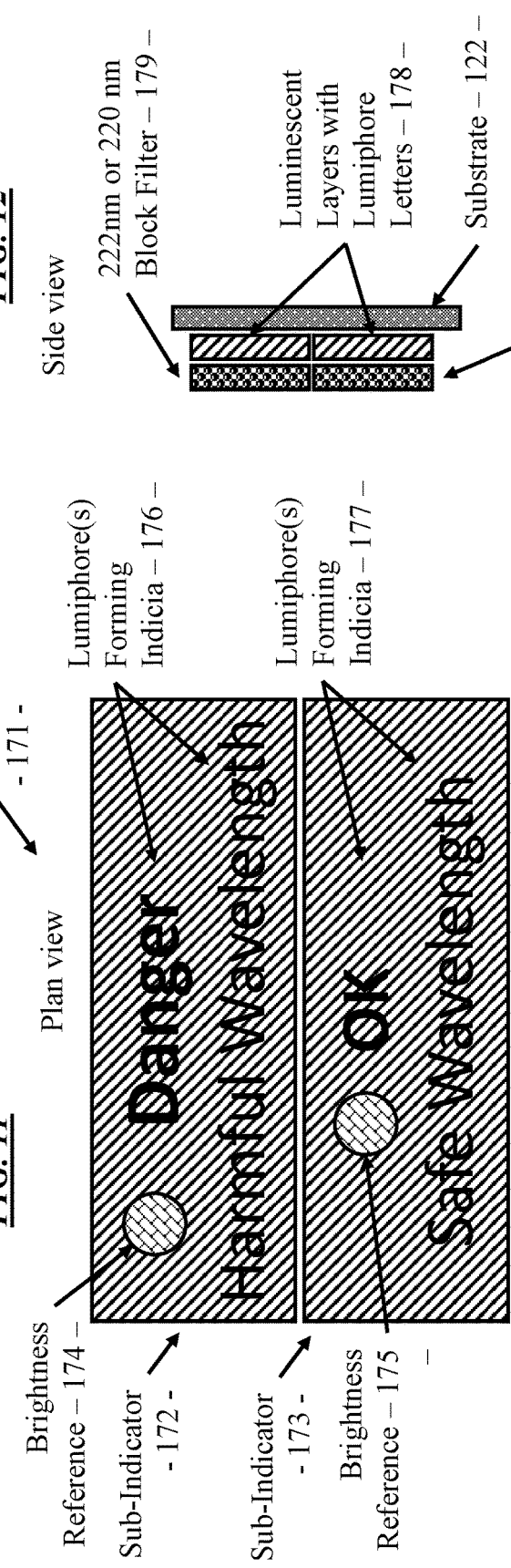
FIG. 11 is a plan view of an example indicator for two different UV bands, where the luminescent layer for each band may be configured to provide an illuminated indicia relative to the respective band.

FIG. 11 is a plan view of an example indicator 171 for two different UV bands, where a portion of the luminescent layer or a separate layer, for each band, may be configured to provide an illuminated indicia relative to the respective band. For a cleansing example, UV having a 222 or 220 nm dominant wavelength (examples of dominant wavelengths in the range of 207 nm to 225 nm) is generally considered relatively safe UV with respect to potential impact on humans. If a 222 or 220 nm UV light source starts emitting other longer wavelengths, such as around 260 nm, the source should be turned off and replaced. The indicator 171 indicates when UV in the safe range is detected, when UV in the unsafe range is detected and relative brightness in each band.

The indicator 171 could be implemented with one brightness reference and two layers or sections of a luminescent layer with indicia to respond to the different UV bands. In the example shown, however, the indicator is implemented more like to sub-indicators 172, 173, wherein the first sub-indicator 172 includes a first brightness reference 174 and the second sub-indicator 173 includes a second brightness reference 175. In any case, each one or more brightness reference may be implemented in any of the various ways described with regard to the earlier examples.

Each sub-indicator 172, 173 includes a luminescent layer or section thereof with lumiphores distributed in a pattern forming appropriate indicia regarding the UV band to be detected so as to output visible light in the shape of the respective indicia when excited by reception of UV. For example, the sub-indicator 172 is configured to detect harmful UV light (e.g. having dominant wavelength(s) outside the 207 nm to 225 nm range), and the lumiphore(s) 176 forming the indicia of that sub-indicator are distributed in the shape of an indication to the effect that "Danger Harmful Wavelength" has been detected or the like when UV light in that band is received and excites the lumiphore(s) 176 in the sub-indicator 172. In such an example, the sub-indicator 173 is configured to detect safe UV light suitable for cleansing (e.g. having dominant wavelength(s) in the 207 nm to 225 nm range), and the lumiphore(s) 177 in that sub-indicator are distributed in the shape of an indication to the effect that a "Safe Wavelength" has been detected or the like when UV light in the safe band is received and excites the lumiphore(s) 177 in the sub-indicator 173. The precise wordings of the indicia are shown by way of non-limiting examples only.

An observer may visually compare intensity of the visible light output from the lumiphores 176 forming the indicia in sub-indicator 172 to intensity of the visible light output from the brightness indicator 174, as in the earlier examples. Similarly, an observer may visually compare intensity of the visible light output from the lumiphores 177 forming the indicia in sub-indicator 173 to intensity of the visible light output from the brightness indicator 175, as in the earlier examples.

Figure 12:
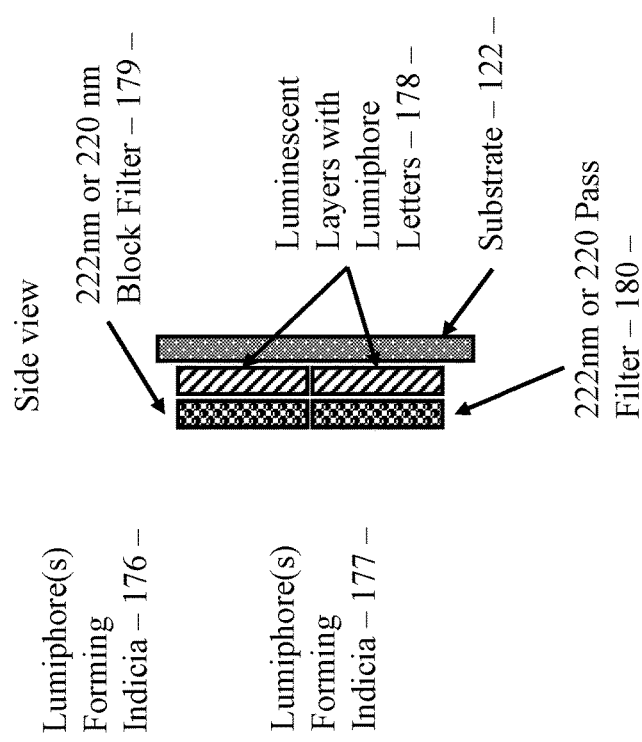
FIG. 12 is a side view showing the luminescent layers of a first implementation of the indicator of FIG. 11, using optical filters.
Figure 13:
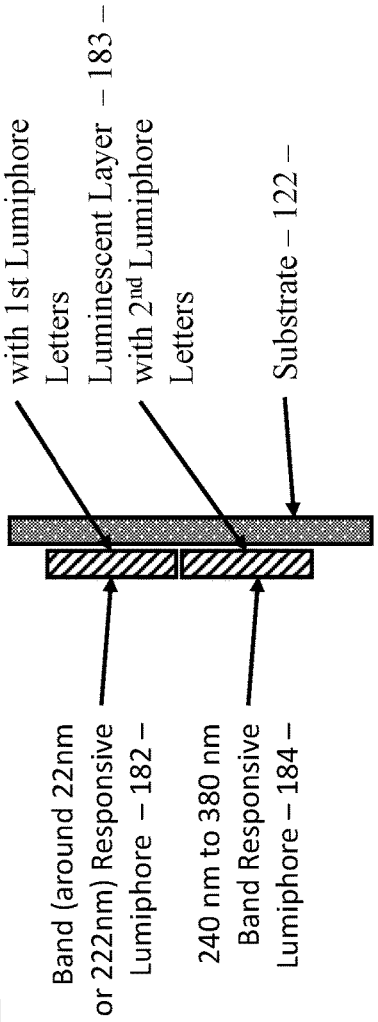
FIG. 13 is a side view showing the luminescent layers of a second implementation of the indicator of FIG. 11, using different lumiphores that are responsive to different bands or ranges of UV light.

The lumiphores for the sub-indicators, for detecting different UV bands may be implemented in various ways, two examples of which are shown in FIGS. 12 and 13.

FIG. 12 is a side view showing the luminescent layers of a first example implementation of the indicator of FIG. 13, which utilizes optical filters to distinguish the harmful and safe UV wavelength bands. The lumiphore lettering is formed in one or two layers 178 on a substrate 122. The substrate 122 may be similar to the substrate in the earlier examples. The lumiphore(s) in layer(s) 178 are the same in that they respond to the same UV wavelength excitation range (e.g. most if not all of the range from 180 nm to 380 nm in the ultraviolet (UV) portion of the spectrum) but are distributed in patterns forming the two different indicia (for example as shown at 176 and 177 in FIG. 11). The lumiphores for the different sub-indicators may be the same, for example so as to produce (e.g., by emitting, reflecting, or a combination of emitting and reflecting) the same converted visible output light color characteristic, or lumiphores for the different sub-indicators may produce different color outputs to help emphasize the harmful versus safe distinction. If they lumiphores produce the same color output, the brightness references 174, 175 may produce visible output light of a color characteristic substantially similar to that of the visible light from the lumiphore(s) 176, 177. If the lumiphores 176, 177 produce different color visible light when excited, the brightness reference 174 may output visible light similar in color to the light output from the lumiphore(s) 176 and the brightness reference 175 may output visible light similar in color to the light output from the lumiphore(s) 177.

Since the lumiphore(s) 178 have the same excitation range, UV filters 179, 180 are provided to distinguish the UV light received by the lumiphore(s) in the different indicia patterns 176, 177 in the two sub-indicators 172, 173. For the harmful wavelength indication, sub-indicator 172 includes a UV filter 179 of a type configured to block UV wavelengths centered around the safe dominant wavelength selected for the cleansing application, e.g. around 220 nm or around 222 nm. Hence, the lumiphores forming the "Danger Harmful Wavelength" indicia 176 would receive and be excited to emit visible light in response only to UV wavelengths outside that safe band. For the safe wavelength indication, sub-indicator 173 includes a UV filter 180 of a type configured to pass only UV wavelengths centered around the safe dominant wavelength selected for the cleansing application, e.g. around 220 nm or around 222 nm. Hence, the lumiphores forming the "OK Safe Wavelength" indicia 177 would receive and be excited to emit visible light only upon receipt of UV wavelengths within that safe band.

FIG. 13 is a side view showing the luminescent layers of a second implementation of the indicator of FIG. 13, using different lumiphores that are responsive to different bands or ranges of UV light. In this example, the indicator would include a first luminescent layer 181 with one or more first lumiphores 182 distributed to form the first indicia 176. The indicator also includes a second luminescent layer 183 with one or more second lumiphores 184 distributed to form the second indicia 184. The first lumiphore(s) 182 would be phosphors or the like configured to have an excitation band around the safe dominant wavelength selected for the cleansing application, e.g. around 220 nm or around 222 nm. Hence, the lumiphores 182 forming the "Danger Harmful Wavelength" indicia 176 would receive and be excited to emit visible light in response only to UV wavelengths outside that safe band. The first lumiphore(s) 182 would be phosphors or the like configured to have an excitation band outside the band for safe UV irradiation, e.g. having an excitation range of 240 nm to 380 nm. The two lumiphores 183, 184 may be configured to output visible light of substantially the same color characteristic or may emit visible light of different color characteristics. The operations/uses of the indicator implementation having the luminescent layers 182, 183 and the brightness references 174, 175 would be substantially the same as discussed earlier relative to the example of FIG. 12.

Figure 14:
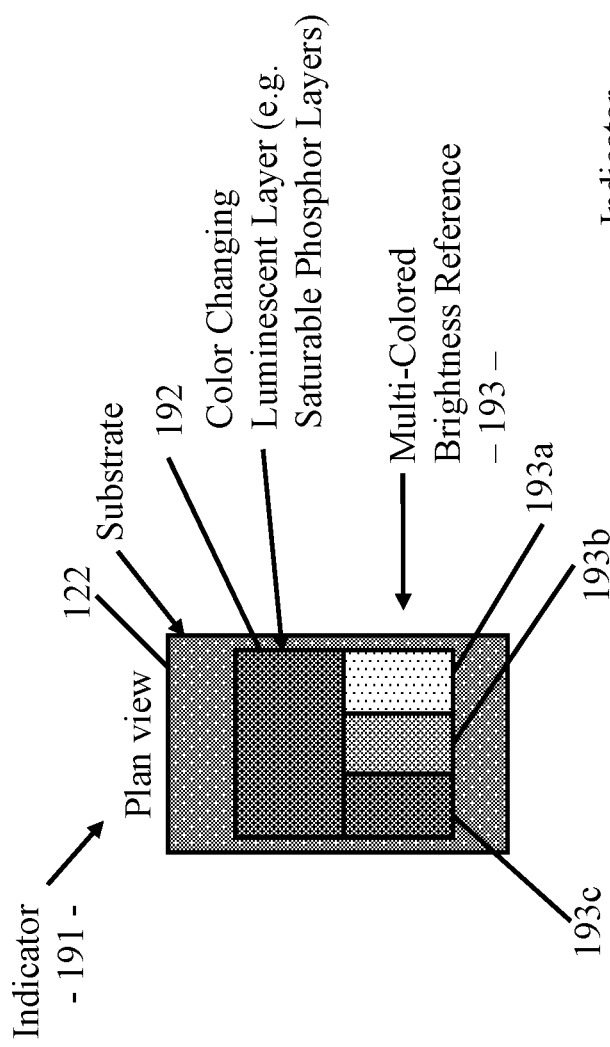
FIGS. 14 and 15 are plan and side views respectively of an example of an indicator using a color changing luminescent layer (e.g. layers containing different saturable passively activated lumiphores) and a brightness reference having strips or the like providing different color references.
Figure 15:
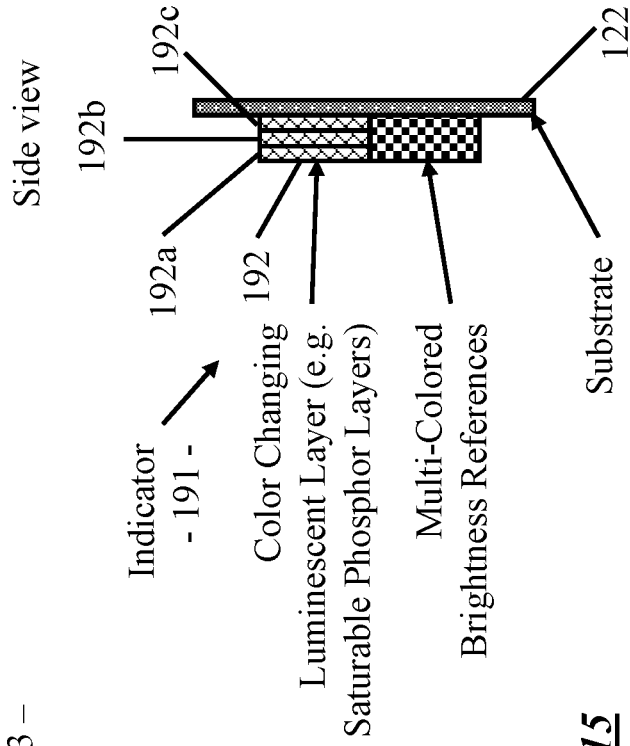

FIGS. 14 and 15 are plan and side views respectively of an example 191 of an indicator using a color changing luminescent layer 192 (e.g. stacked layers as shown in FIG. 15 containing different saturable passively activated lumiphores). Nano-phosphors, for example, can be tailored to have a similar UV excitation band but may have different saturations and to provide different color emissions when excited by received UV light in the excitation band. The indicator 191 also includes a multi-colored brightness reference 193 that can include a number of multi-colored brightness reference strips 193A-C corresponding in number and approximate color to the different light outputs from the color changing luminescent layer 192. In FIGS. 14-15, the multi-colored brightness reference 193 is primarily a color reference, but can also be a brightness reference, or a combination of a color reference and a brightness reference. Although shown as distinct layers in FIG. 14, the multi-colored brightness reference strips 193A-C can be uniform in a vertical direction, but have a gradient in the horizontal direction.

The luminescent layer 192 includes a number of sub-layers each having a different saturable lumiphore. In the example of FIGS. 14 and 15, the color-changing luminescent layer 192 includes three sub-layers 192*a* to 192*c* each having a different saturable lumiphore, although there may be as few as two such layers or more than three such layers. The different saturable lumiphores in the sub-layers, for example, may be different nano-phosphors, configured with the same excitation band but different saturations. The different saturable lumiphores in the sub-layers in such an example are also configured to emit different colors of light when respectively excited. The drawing in FIG. 15 shows the sub-layers 192*a* to 192*c* stacked on each other on the substrate 122. It should be understood that the bottom layer in this example 192C can be saturable or non-saturable. A saturable absorber absorbs light until it becomes saturated and can no longer absorb received light (e.g., sanitation light) above its saturation intensity. The saturable absorber is then translucent or transparent to the received light above its saturation intensity. The saturation intensity may not be an abrupt cutoff, but a function. A non-saturable absorber absorbs all received light. The absorber can include dyes, lumiphores, etc., as described above.

In the illustrated three layer example, one of the sub-layers (e.g. 192*a*) of the indicator 191 includes a first passively activated saturable lumiphore configured to saturate and convert received UV light up to a first intensity to first visible light and causes the luminescent layer 192 to output visible light of a first color characteristic. Another of the sub-layers (e.g. 192*b*) of the indicator 191 includes a second passively activated lumiphore configured to convert received UV light exceeding the first intensity to second visible light of a second color characteristic. The second threshold intensity is higher than the first threshold intensity, and the second visible light or combination of the first and second visible lights causes the color changing luminescent layer 192 to output visible light of a second color characteristic. The second color characteristic is visibly different from the first color characteristic. The multi-colored brightness reference 193 includes a first reference 193*a* configured to emit light at least substantially of the first color characteristic in a first region of the multi-colored brightness reference 193. The multi-colored brightness reference 193 further includes a second reference 193*b* configured to emit light at least substantially of the second color characteristic in a second region of the multi-colored brightness reference.

Additionally in some examples, a third sub-layer 192*c* can further comprise a third passively activated lumiphore configured to convert received UV light exceeding the second intensity to third visible light of a third color characteristic. The multi-colored brightness reference 193 includes a third reference 193*c* configured to emit light at least substantially of the third color characteristic in a third region of the multi-colored brightness reference 193. The first, second, and third passively activated saturable lumiphore can include first, second, and third nano-phosphors.

For example, when sanitation light (e.g., UV light) is shined on a saturable lumiphore, such as the color changing luminescent layer 192*a*, the saturable lumiphore glows. When enough sanitation light is shined and a saturation intensity is reached, the first saturable sub-layer 192*a* reaches saturation and does not absorb excess sanitation light above the saturation intensity, meaning the first saturable sub-layer 192*a* does not glow any brighter. Hence, the excess unabsorbed sanitation light (e.g., excessive received UV light) passes to the second non-saturable sub-layer 192*b*. The second non-saturable sub-layer 192*b* absorbs the excess sanitation light above the sanitation light intensity absorbed in the saturable first sub-layer 192*a* and glows (e.g., fluoresces). In a two-level color changing luminescent layer 192 example, where the first saturable sub-layer 192*a* is green and the second non-saturable sub-layer is red 192*b*, the two-level color changing luminescent layer 192 can be changed to emit light from greenish-yellow to reddish-yellow, etc. depending on the levels of the intensity of the sanitation light and the saturation intensity.

There may be more saturable lumiphores, e.g. three as shown or four, or five, etc. In the example shown, when the second sub-layer 192*b* saturates and behaves as a saturable lumiphore, another one of the sub-layers (e.g. 192*c*) of the indicator 191 can include a third lumiphore configured convert received UV light above a third intensity to third visible light. The third intensity is higher than the second intensity (and thus also higher than the first intensity), and the third visible light or combination of the first, second and third visible lights causes the color changing luminescent layer 192 to output visible light of a third color characteristic, which is visibly different from the first color characteristic and from the second color characteristic.

The side view of FIG. 15 shows stacked layers 192*a* to 192*c* of nano-phosphors as the first, second and third saturable lumiphore. As each lumiphore receives UV or saturates (as received UV reaches the respective saturation level), each nano-phosphor sub-layer 192*a-c* emits the respective visible light and continues to emit the respective visible light. In the example of FIG. 15, the top first nano-phosphor sub-layer 192*a* and second nano-phosphor sub-layer 192*b* are saturable, but the bottom nano-phosphor sub-layer 192*c* does not need to be saturable (e.g., is non-saturable). It should be understood that as described herein, the sub-layers 192*a-c* of the color changing luminescent layer 192 do not have to be the same type. For example, the sub-layers 192*a-c* can be different, such as nano-phosphor, rare earth, or others. Alternatively or additionally, the sub-layers 192*a-c* can be a mixture of nano-phosphor, rare earth, etc. While the sub-layers 192*a*-*c* can be distinct, the sub-layers 192*a*-*c* can be gradients in depth with a continuous transition in between. For example, the top sub-layer 192*a* can be a first color and the second sub-layer 192*b* can be another color.

In the illustrated stacked arrangement, when the received UV light does not exceed the first intensity, the first nano-phosphor is not saturated (e.g. sub-layer 192*a* assuming a reflective implementation of the substrate 122). Thus, only the one visible light is emitted from overall color changing luminescent layer 192 to produce the output of the first color characteristic from sub-layer 192*a*. However, when one or more nano-phosphors are saturated, the visible lights from the nano-phosphors are added to form a composite light output from overall color changing luminescent layer 192 as some light from inner sub-layer(s) 192*a* passes through one or more outer sub-layers 192*b*-*c*. The combination of two visible lights when only one nano-phosphor is saturated (received UV light exceeds the first intensity, but does not exceed the second intensity), produces combined light from two sub-layers 192*a*-*b* of the second color characteristic from overall luminescent layer 192. When the received UV light exceeds the second intensity, the combined visible lights from all three sub-layers 192*a*-*c* produces a combined light output of the third color characteristic from overall color changing luminescent layer 192.

The indicator 191 in the example of FIGS. 14 and 15 includes a multi-colored brightness reference 193 having strips or the like as individual references for providing different color references to correspond to different levels of brightness, so that when the light output of the luminescent layer 192 changes colors as the intensity of the UV light changes the individual references provide different colors and intensities for comparison purposes. Although there may be two or more individual references of different colors, the example multi-colored brightness reference 193 shows three individual multi-colored brightness reference strips 193*a* to 193*b*. Except for the differences in visible output spectra, each individual one of the reference strips 193*a* to 193*b* may be implemented using any of the various techniques for implementing a brightness reference in the discussions above relative to FIGS. 1 to 13. For convenience, however, each of the multi-colored brightness reference strips 193*a* to 193*b* is shown as an individual layer or sections of a layer with a different lumiphore outputting (e.g., by reflecting) different visible light color in response to visible light received from the luminaire (having a visible light excitation band), e.g. each having a lumiphore like that in the brightness reference 136 in the example of FIGS. 2 and 3 except having a different color light output band.

In FIGS. 14-15, the multi-colored brightness reference 193 is configured as a reflector instead of a color changing luminescent layer 192. Hence, the example multi-colored brightness reference 193 is mounted in visible proximity to the at least one luminescent layer 192 that provides the color changing output in response to different levels of received UV. The example multi-colored brightness reference 193 includes first, second and third individual references 193*a* to 193*c*, although there may be only two such individual references or there may be four, five or more such individual references. The first reference, shown for example as a first reference strip 193*a*, is configured to reflect light of the first color characteristic in a first region of the overall brightness reference 193. The second reference, shown for example as a second reference strip 193*b*, is configured to reflect light of the second color characteristic in a second region of the brightness reference 193. If provided, the third reference, shown for example as a third reference strip 193*c*, is configured to reflect light of the third color characteristic in a third region of the multi-colored brightness reference 193. It should be understood that the multi-colored brightness reference 193 configured as a reflector in FIGS. 14-15 can be replaced by an emitter (see element 154 in FIG. 7 and elements 124 and 136 in FIGS. 2-6).

With the indicator example 191 of FIGS. 14 and 15, the color output of the UV responsive color changing luminescent layer 192 would exhibit light of different colors based on saturations of different lumiphores at two, three or more different intensity levels. In a two-level, three-level, or other multi-level color changing luminescent layer 192 or multi-colored brightness reference 193, the saturation intensity of each level is selected to provide varying colors depending on the intensity of the sanitation light. An observer could visibly compare the color of the output of the UV responsive luminescent layer 192 to the two three or more colors of the strips of the multi-colored brightness reference 193, a color changing luminescent layer 192 (e.g., saturable or non-saturable phosphor layers 192*a*-*c*), or a combination of the multi-colored brightness reference 193 and the color changing luminescent layer 192 to visually determine the relationship of the current intensity of UV light received from the luminaire (FIG. 1) relative to the various intensity thresholds. For example, one of the thresholds and a corresponding reference color may indicate a desired intensity level for a cleansing application. Alternatively, intensities at the various thresholds may be suitable for cleansing but may indicate that different exposure times are needed at the respective intensities to achieve a suitable cleansing dosage.

In most of the examples of usage described above, the observer has been a person. Observation, however, may be assisted or performed by a device or system equipped with a camera or the like. A mobile device with a suitable application program, for example, could take an image of the indicator and compare the light from the lumiphore(s) to the intensity and/or color of the brightness reference.

Figure 16:
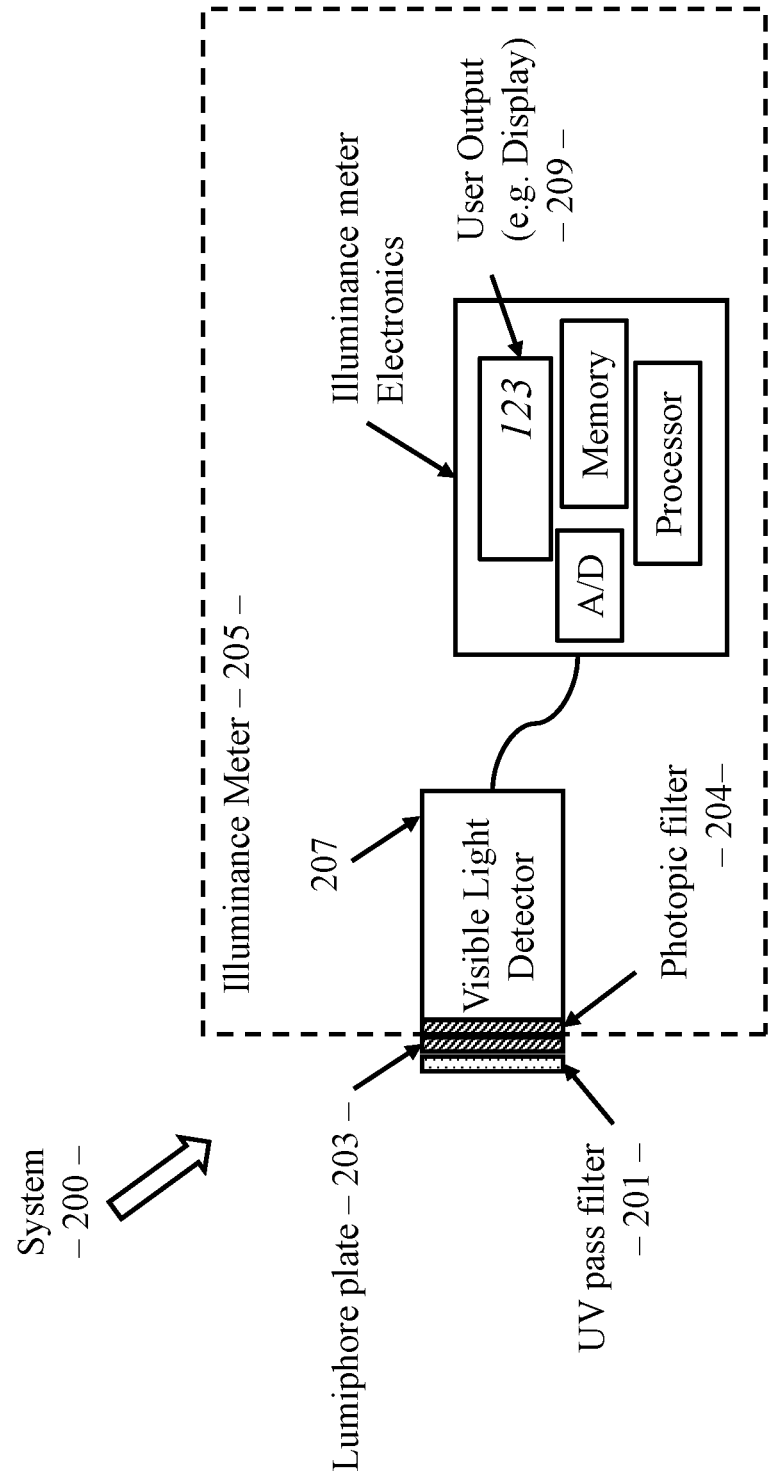
FIG. 16 shows a side view of a filter and a phosphor bearing plate and shows a block diagram of a visible light meter capable of illuminance measurement, coupled together with the phosphor bearing plate so that the meter outputs a proportional representation of intensity of UV light received at the phosphor bearing plate via the filter.

FIG. 16 shows a system 200 for measuring UV illuminance or intensity, for example, as received from a luminaire like that shown in FIG. 1. The drawing includes a side view of a UV pass filter 201, a photopic filter 204, and a lumiphore bearing plate 203 and shows a block diagram of a visible light meter 205 capable of illuminance measurement, coupled together with the lumiphore bearing plate 203 so that the meter 205 outputs a proportional representation of intensity of UV light received at the lumiphore bearing plate 203 via the UV pass filter 201 and the photopic filter 204. An example of the visible light meter 205 that includes a photopic filter 204 is a Konica-Minolta CL 200. Visible light meter 205 is calibrated for visual photopic measurements, such as illuminance, e.g., foot-candles or lux.

In the example, the light meter 205 includes an optical input, such as the illustrated visible light detector 207 and a user output 209. The detector may be one or more photodiodes or the like. The detector 207 is configured to produce a signal proportional to intensity of visible light received at the input surface of the detector. The user output 209 is shown by way of non-limiting example as a display, although persons skilled in the art will recognize that the meter may utilize audio, tactile or other output technologies in place of or in addition to the display.

In the example, the system 200 also has a luminescent layer included as part of the lumiphore plate 203. The plate 203 may take the form of a substrate and luminescent layer with one or more lumiphores like in the earlier examples. In system 100 the luminescent layer on or in plate 203 is configured for optical coupling to the detector 207 serving as the optical input of the light illuminance meter 205. As in earlier examples, the luminescent layer has a passively activated lumiphore that converts any received UV light in at least a portion of the 180 nm to 380 nm UV wavelength range to light having one or more dominant wavelengths in the visible light range.

The light meter 205 is configured to measure intensity of the visible converted light from the passively activated lumiphore received through the optical input (e.g. via detector 207) and provide a representation of the measured intensity via the user output 209 as a representation of intensity of the received UV light. The electronics of the meter 205 may be implemented and configured in a variety of ways. In the example, the electronics are digital and programmable and include for example, a processor, an analog-to-digital converter (A/D) to supply a digitized version of the signal from the detector 207 to a processor, and a memory storing digital data as well as programming executable by the processor to implement the operations of the meter 205.

With reference to FIGS. 1 and 16, operation may involve the luminaire 101 emitting visible light for general illumination of a space from light source 102. The luminaire 101 also emits UV light from source 204. The UV light has a dominant wavelength in a range from 180 nm to 380 nm, for example, so as to implement a sanitation application in the space. The method of operation further entails exposing the luminescent material in or on the plate 203 to the UV light emission from the luminaire 101. To avoid excitation of the detector by visible light from the luminaire, the filter 201 passes UV light to the lumiphore plate 203 but blocks other light including visible light that might otherwise pass through the plate 203 to the detector 207.

The detector 207 receives and senses the visible light produced by conversion of received UV into visible light by the passively activated lumiphore of the luminescent material on or in the plate 203. The user output 209 provides a basis for observation so that the user can determine intensity of the UV light emission from the luminaire based at least in part on intensity of the light having one or more dominant wavelengths in the visible light range from the passively activated lumiphore. In the specifically illustrated example, the processor would respond to the digitized signal from the detector 207 and control the display (of output 209) to generate a visible readout of illuminance corresponding to the intensity of UV light at the lumiphore plate 203.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like, whether or not qualified by a term of degree (e.g. approximate, substantially or about), may vary by as much as ±10% from the recited amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected may lie in less than all features of any single disclosed example. Hence, the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An indicator, comprising:
    a luminescent layer, configured for exposure of at least a portion of the luminescent layer to light from a luminaire configured to emit ultraviolet (UV) light having a dominant wavelength in a range from 180 nanometers (nm) to 380 nm,
    wherein the luminescent layer comprises a passively activated lumiphore configured to convert received UV light in at least a portion of the 180 nm to 380 nm UV wavelength range to light having one or more dominant wavelengths in the visible light range; and
    a brightness reference, mounted in visible proximity to the luminescent layer, configured to produce visible light of a predetermined intensity for comparison to intensity of visible converted light from the passively activated lumiphore during reception of the UV light by the passively activated lumiphore.

2. The indicator of claim 1, wherein:
    the passively activated lumiphore is configured to emit visible light of a predetermined color characteristic; and
    the brightness reference is further configured to produce visible light of a color characteristic at least substantially similar to the predetermined color characteristic.

3. The indicator of claim 1, wherein the brightness reference comprises another luminescent layer, configured to produce visible light of the predetermined intensity, the other luminescent layer comprising another passively activated lumiphore configured to convert at least some visible light received from the luminaire to visible light of a predetermined color characteristic at the predetermined intensity.

4. The indicator of claim 1, wherein the passively activated lumiphore comprises a phosphorescent material configured to discharge over time after ceasing to receive UV light, so as to cease emission of the visible light of the predetermined color characteristic after a predetermined time delay indicative a period after which UV light emission should be restarted.

5. The indicator of claim 1, wherein the brightness reference comprises:
an artificial light source configured to produce the visible light of the predetermined intensity in response to applied electrical power; and
a driver circuit configured to apply the electrical power to the light source.

6. The indicator of claim 5 further comprising a substrate, wherein:
the luminescent layer is supported by the substrate;
the brightness reference further comprises a user input for receipt of an intensity setting for the artificial light source; and
the driver circuit is further configured to set a level of the electrical power applied to the light source in response to the intensity setting received via the user input.

7. The indicator of claim 5, wherein the artificial light source comprises:
a visible light source driven by the applied electrical power; and
another luminescent layer, configured to produce visible light of the predetermined intensity, the other luminescent layer comprising another passively activated lumiphore configured to convert visible light received from the visible light source to visible light of a predetermined color characteristic at the predetermined intensity.

8. The indicator of claim 5, wherein the artificial light source comprises:
a UV light source driven by the applied electrical power and positioned to direct UV light to a section of the luminescent layer such that the passively activated lumiphore in the section of the luminescent layer converts UV light from the UV light source into the visible light of the predetermined intensity for the comparison.

9. The indicator of claim 1, further comprising:
a first filter associated with the luminescent layer to limit UV light applied to a first section of the luminescent layer to a first part of the 180 nm to 380 nm UV wavelength range; and
a second filter associated the luminescent layer to limit UV light applied to a second section of the luminescent layer to a second part of the UV wavelength range outside the first part of the UV wavelength range.

10. The indicator of claim 9, wherein the first part of the UV wavelength range includes a band of wavelengths around a dominant wavelength in a range from 207 nm to 225 nm.

11. The indicator of claim 9, wherein:
the brightness reference is mounted in visible proximity to the first section of the luminescent layer; and
the indicator further comprises another brightness reference, mounted in visible proximity to the second section of the luminescent layer, configured to produce visible light of a predetermined intensity for comparison to intensity of visible converted light from the second section of the luminescent layer during reception of the UV light.

12. The indicator of claim 1, wherein the luminescent layer comprises:
a first section having a first type passively activated lumiphore configured to convert received UV light in a first part of the UV wavelength range to light having one or more dominant wavelengths in the visible light range; and
a second section having a second type passively activated lumiphore configured to convert received UV light in a second part of the UV wavelength range outside the first part of the UV wavelength range to light having one or more dominant wavelengths in the visible light range.

13. The indicator of claim 12, wherein the first part of the UV wavelength range includes a band of wavelengths around a dominant wavelength in a range from 207 nm to 225 nm.

14. The indicator of claim 12, wherein:
the brightness reference is mounted in visible proximity to the first section of the luminescent layer; and
the indicator further comprises another brightness reference, mounted in visible proximity to the second section of the luminescent layer, configured to produce visible light of a predetermined intensity for comparison to intensity of visible converted light from the second section of the luminescent layer during reception of the UV light.

15. A system comprising the indicator of claim 1 and the luminaire.

16. The system of claim 15, wherein the luminaire comprises:
a first source of visible light for general illumination; and
a second source of the UV light having the dominant wavelength in the range from 180 nm to 380 nm.

17. An indicator, comprising:
at least one luminescent layer, configured for exposure of at least a portion of the at least one luminescent layer to light from a luminaire configured to emit ultraviolet (UV) light having a dominant wavelength in a range from 180 nanometers (nm) to 380 nm,
the at least one luminescent layer comprising:
a first passively activated saturable lumiphore configured to saturate and convert received UV light up to a first intensity to first visible light that causes the luminescent layer to output visible light of a first color characteristic; and
a second passively activated lumiphore configured to convert received UV light exceeding the first intensity to second visible light of a second color characteristic, wherein:
the second intensity is higher than the first intensity,
the second visible light or a combination of the first visible light and the second visible light causes the luminescent layer to output visible light of a second color characteristic, and
the second color characteristic is visibly different from the first color characteristic; and
a multi-colored brightness reference, mounted in visible proximity to the at least one luminescent layer, wherein the multi-colored brightness reference comprises:
a first reference configured to emit light at least substantially of the first color characteristic in a first region of the multi-colored brightness reference; and
a second reference configured to emit light at least substantially of the second color characteristic in a second region of the multi-colored brightness reference.

18. The indicator of claim 17, wherein:
the at least one luminescent layer further comprises a third passively activated lumiphore configured to convert received UV light exceeding the second intensity to third visible light of a third color characteristic;

the multi-colored brightness reference includes a third reference configured to emit light at least substantially of the third color characteristic in a third region of the multi-colored brightness reference;

the first, second, and third passively activated saturable lumiphore comprise first, second, and third nano-phosphors.

19. The indicator of claim 17, further comprising a substrate, wherein the at least one luminescent layer comprises:

a first layer mounted on a surface of the substrate and containing one of the first and second passively activated saturable lumiphores; and a second layer mounted on a surface of the first layer opposite the surface of the substrate and containing the other one of the first and second passively activated saturable lumiphores.

20. A measurement system, comprising:

a light meter calibrated for visual photopic measurements, the light meter having an optical input and a user output;

a luminescent layer configured for optical coupling to the optical input of the light meter, the luminescent layer comprising a passively activated lumiphore configured to convert received ultraviolet (UV) light in at least a portion of the 180 nm to 380 nm UV wavelength range to light having one or more dominant wavelengths in the visible light range; and a UV-pass filter optically coupled to supply UV light to the luminescent layer, the UV-pass filter being configured to block visible light wavelengths, wherein the light meter is configured to measure intensity of the visible converted light from the passively activated lumiphore received through the optical input and provide a representation of the measured intensity via the user output as a representation of intensity of the received UV light.

21. A method, comprising steps of:

emitting, from a luminaire, visible light for general illumination of a space;

implementing a sanitation application in the space by emitting, from the luminaire, ultraviolet (UV) light having a dominant wavelength in a range from 180 nm to 380 nm;

in the space, exposing a luminescent material to the UV light emission from the luminaire, the luminescent material comprising a passively activated lumiphore configured to convert received UV light in at least a portion of the 180 nm to 380 nm UV wavelength range to light having one or more dominant wavelengths in the visible light range; and providing, for observation of a user, a basis to determine intensity of the UV light emission from the luminaire based at least in part on intensity of the light having one or more dominant wavelengths in the visible light range from the passively activated lumiphore.

22. The method of claim 21, wherein the step of providing the basis to determine intensity of the UV light emission comprises emitting visible reference light of a predetermined perceptible characteristic for comparison to a corresponding perceptible characteristic of visible converted light from the passively activated lumiphore during reception of the UV light by the passively activated lumiphore.

23. The method of claim 21, wherein the step of providing the basis to determine intensity of the UV light emission comprises:

using a visible light meter to measure intensity of the visible converted light from the passively activated lumiphore received through an optical input of the light meter; and providing a representation of the measured intensity via a user output of the light meter as a representation of intensity of the received UV light.

\* \* \* \* \*